(12) United States Patent
Grashow et al.

(10) Patent No.: US 11,992,616 B2
(45) Date of Patent: May 28, 2024

(54) RESPIRATORY INTERFACE DEVICE INCLUDING CUSTOM FEATURES

(71) Applicant: KONINKLIJKE PHILIPS N.V., Eindhoven (NL)

(72) Inventors: Jonathan Sayer Grashow, Pittsburgh, PA (US); Lauren Patricia Chodkowski, Pittsburgh, PA (US); David W. Smith, Oakmont, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 219 days.

(21) Appl. No.: 17/324,273

(22) Filed: May 19, 2021

(65) Prior Publication Data

US 2021/0268219 A1 Sep. 2, 2021

Related U.S. Application Data

(62) Division of application No. 16/061,678, filed as application No. PCT/EP2016/081095 on Dec. 15, 2016, now abandoned.
(Continued)

(51) Int. Cl.
*A61M 16/06* (2006.01)
*A61B 5/107* (2006.01)
(Continued)

(52) U.S. Cl.
CPC ............. *A61M 16/06* (2013.01); *A61B 5/107* (2013.01); *A61M 16/0605* (2014.02); *A61M 16/0622* (2014.02); *A61M 16/0683* (2013.01); *A61M 16/0688* (2014.02); *A61M 16/0694* (2014.02); *B33Y 10/00* (2014.12); *B33Y 80/00* (2014.12); *G06V 40/166* (2022.01); *G16H 20/40* (2018.01); *G16H 40/60* (2018.01); *A61M 16/0616* (2014.02); *A61M 16/0633* (2014.02); *A61M 2016/0661* (2013.01); *A61M 16/0816* (2013.01); *A61M 16/0858* (2014.02); *A61M 16/0875* (2013.01); *A61M 2016/1025* (2013.01); *A61M 2016/103* (2013.01); *A61M 16/105* (2013.01); *A61M 16/1095* (2014.02); *A61M 16/208* (2013.01); *A61M 2202/0225* (2013.01);
(Continued)

(58) Field of Classification Search
CPC ...... A61M 2016/0661; A61M 2207/00; A61M 16/06; A61M 16/0605; A61M 16/0616; A61M 16/0622; G06V 40/16–179
See application file for complete search history.

(56) References Cited

U.S. PATENT DOCUMENTS 5,538,000 A 7/1996 Rudolph
5,832,918 A 11/1998 Pantino
(Continued)

FOREIGN PATENT DOCUMENTS

WO 0038772 A1 7/2000
WO 2004056409 A2 7/2004
(Continued)

*Primary Examiner* — Joseph D. Boecker
(74) *Attorney, Agent, or Firm* — Michael W. Haas

(57) ABSTRACT

A respiratory interface device is provided that includes a cushion and a faceplate. The cushion is structured to be coupled to the faceplate. The faceplate includes a peripheral end and a number of custom features. The cushion is coupled to the faceplate adjacent the faceplate peripheral end.

5 Claims, 17 Drawing Sheets

Related U.S. Application Data

(60) Provisional application No. 62/268,043, filed on Dec. 16, 2015.

(51) Int. Cl.
    *A61M 16/08* (2006.01)
    *B33Y 10/00* (2015.01)
    *B33Y 80/00* (2015.01)
    *G06V 40/16* (2022.01)
    *G16H 20/40* (2018.01)
    *G16H 40/60* (2018.01)
    *A61M 16/10* (2006.01)
    *A61M 16/20* (2006.01)

(52) U.S. Cl.
    CPC . *A61M 2205/3303* (2013.01); *A61M 2205/59* (2013.01); *A61M 2207/00* (2013.01); *A61M 2207/10* (2013.01); *A61M 2230/06* (2013.01); *A61M 2230/432* (2013.01); *A61M 2230/435* (2013.01)

(56) References Cited

U.S. PATENT DOCUMENTS

| | | | |
|---|---|---|---|
| 6,196,223 B1 * | 3/2001 | Belfer | A61M 16/0616 128/206.25 |
| 2004/0133604 A1 * | 7/2004 | Lordo | G16H 10/60 |
| 2006/0023228 A1 | 2/2006 | Geng | |
| 2008/0060652 A1 * | 3/2008 | Selvarajan | A61M 16/0683 128/206.21 |
| 2009/0050156 A1 | 2/2009 | Reid | |
| 2011/0220112 A1 | 9/2011 | Connor | |
| 2011/0232647 A1 | 9/2011 | Ho | |
| 2011/0240030 A1 | 10/2011 | Margaria | |
| 2011/0259337 A1 | 10/2011 | Souza | |
| 2012/0204874 A1 | 8/2012 | Sofranko | |
| 2014/0209098 A1 | 7/2014 | Barbara | |
| 2014/0261430 A1 | 9/2014 | Davis | |
| 2014/0299134 A1 * | 10/2014 | Matula | A61M 16/0622 128/205.25 |
| 2014/0326243 A1 | 11/2014 | Van Bree | |
| 2015/0217518 A1 * | 8/2015 | Chun | A61M 16/06 700/98 |
| 2016/0361511 A9 * | 12/2016 | Karpas | A61M 16/0683 |
| 2019/0232013 A1 * | 8/2019 | Yu | A61B 5/1077 |

FOREIGN PATENT DOCUMENTS

| | | | |
|---|---|---|---|
| WO | 2007139531 A1 | 2/2007 | |
| WO | 2013064931 A1 | 5/2013 | |
| WO | 2014075797 A1 | 5/2014 | |
| WO | WO-2014091370 A1 * | 6/2014 | A61M 16/06 |
| WO | 2014180657 A2 | 11/2014 | |
| WO | 2015017829 A2 | 2/2015 | |
| WO | 2015195303 A1 | 12/2015 | |
| WO | WO-2015195303 A1 * | 12/2015 | A62B 23/025 |
| WO | 2016000040 A1 | 1/2016 | |

* cited by examiner

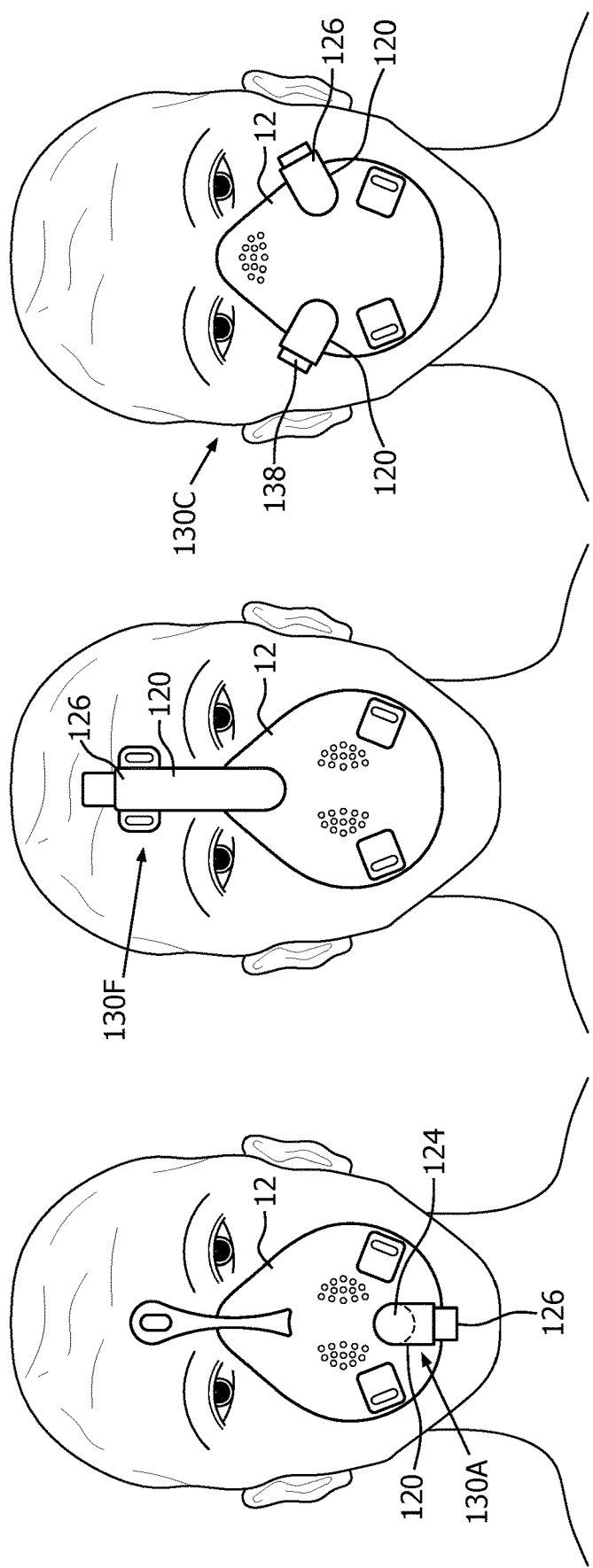

RESPIRATORY INTERFACE DEVICE INCLUDING CUSTOM FEATURES

CROSS-REFERENCE TO RELATED APPLICATIONS

This patent application is a Divisional of U.S. patent application Ser. No. 16/061,678, filed on Jun. 13, 2018, which claims the priority benefit claims under 35 U.S.C. § 119(e) of U.S. Provisional Application No. 62/268,043, filed on Dec. 16, 2015, the contents of which are herein incorporated by reference.

BACKGROUND OF THE INVENTION

1. Field of the Invention

The present invention relates to respiratory interface devices for transporting a gas to and/or from an airway of a user and, in particular, to a faceplate including features with custom characteristics.

2. Description of the Related Art

A variety of respiratory interface devices are known in the art. These interface devices include a mask, or respiratory interface device, through which gases can be provided (e.g., at a positive pressure) for consumption by the user. Such masks include, without limitation, nasal/oral masks that fit over the mouth and nose of the user, nasal masks which fit over only the nose of the user, and nasal pillows with prongs which fit into the nares of the user. It is known to maintain such interfaces on the face of a user by a headgear that wraps around the head of the user. The uses for such interface devices include high altitude breathing (aviation applications), swimming, mining, firefighting and various medical diagnostic and therapeutic applications.

One requisite of many of these interface devices, particularly medical respiratory interface devices, is that they provide an effective fit against the user's face to limit or prevent leakage of the gas being supplied. In an exemplary embodiment, masks include a rigid faceplate and a resilient, flexible cushion. The cushion is coupled to the faceplate. Thus, the rigid faceplate provides support and maintains the general shape of the cushion. The cushion is structured to contact the user's face.

With the exception of custom made interface devices, faceplates and cushions are mass produced and are therefore generic. That is, the faceplates and cushions are not generally customized for a specific user. Masks including such faceplates and cushions provide a generally continuous seal against the user's face. A customized mask, however, provides a more complete seal.

A customized mask is based on a user's facial contours. That is, a user has their face scanned, or otherwise modeled, to create a user's 3D surface profile. The user's 3D surface profile is used to design a custom mask structured to substantially match the contours of the user's face. The custom mask is then produced for that user. Such a custom mask is structured to better engage the contours of the user's face. A custom mask may include a unitary faceplate and cushion. That is, the faceplate and cushion are molded as a single piece. Such custom masks are expensive. Moreover, the cushion is subject to wear and tear. Thus, when the cushion deteriorates, a new custom mask must be created.

Some custom masks utilize a custom cushion. That is, the faceplate is generic, but a custom cushion is created for a user based on a user's 3D surface profile, e.g., a facial profile. A user may have multiple cushions created, thereby reducing cost, but custom cushions are still expensive. Further, the user's supply of custom cushions will eventually need to be replenished. This means that either the manufacturer will need to maintain the molds for each user, or, the user will need to have a new mold made each time their supply of cushions needs to be replenished.

Such custom masks are structured to provide a cushion that is custom made for the user. These fabrication methods, however, are not addressed to other respiratory interface device features. That is, the mask also includes a number of features, such as, but not limited to, support assembly couplings and fluid couplings. The characteristics of such respiratory interface device features are either set as default characteristics, or, are adjusted according to a computer model of the user's 3D surface profile. For example, WO 2014/075797 discloses positioning an attachment means for attachment of a supplementary device at an optimal location for each individual, taking into account irregularities of the face. Such default or computer adjusted characteristics do not, however, account for the user's preferences, i.e., these masks do not include features with custom characteristics.

SUMMARY OF THE INVENTION

One embodiment of the presently disclosed concept provides a respiratory interface device including a cushion and a faceplate. The cushion is structured to be coupled to the faceplate. The faceplate includes a peripheral end and a number of custom features. The cushion is coupled to the faceplate adjacent the faceplate peripheral end.

Another embodiment of the presently disclosed concept provides a method of making a respiratory interface device including a number of custom features. The method of making a respiratory interface device includes acquiring a 3D surface profile of a user's face, selecting characteristics for a number of custom features, and producing a respiratory interface device including custom features with the selected custom feature characteristics.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 17 is a schematic front view of a respiratory interface device with a custom fluid coupling in a lower location;

FIG. 18 is a schematic front view of a respiratory interface device with a custom fluid coupling in an upper location;

FIG. 19A is a schematic front view of a respiratory interface device with a custom Tube-In-Headgear (TIHM) fluid coupling in lateral locations.

DETAILED DESCRIPTION OF EXEMPLARY EMBODIMENTS

Figure 1:
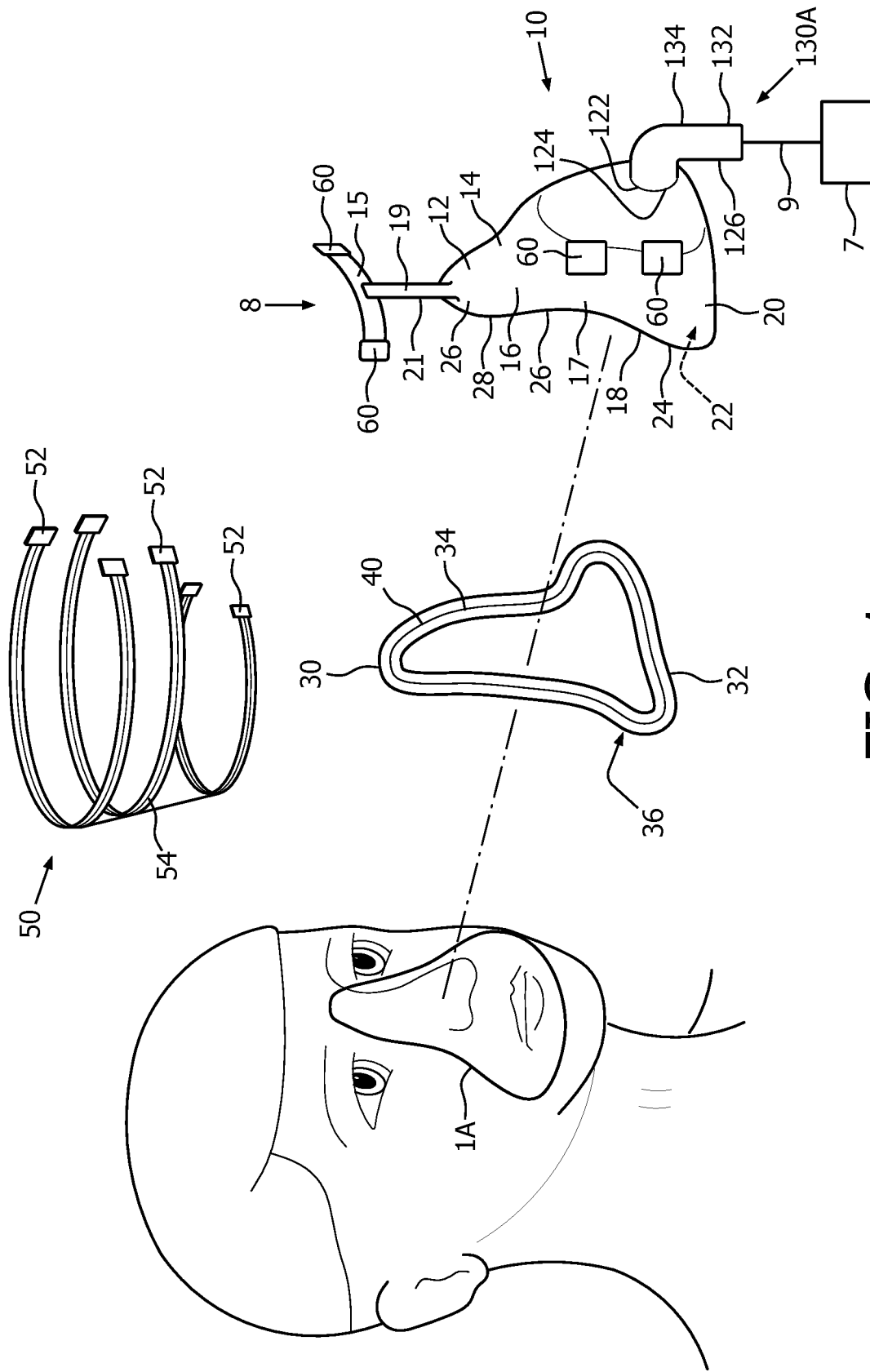
FIG. 1 is a schematic view of a respiratory interface assembly including a respiratory interface device.
Figure 4:
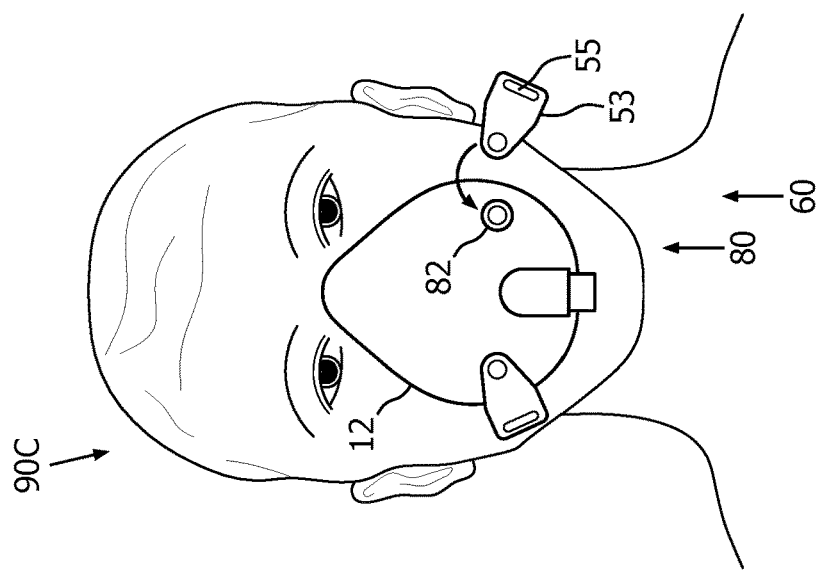
FIG. 4 is a schematic front view of a respiratory interface device with magnetic clips.
Figure 3:
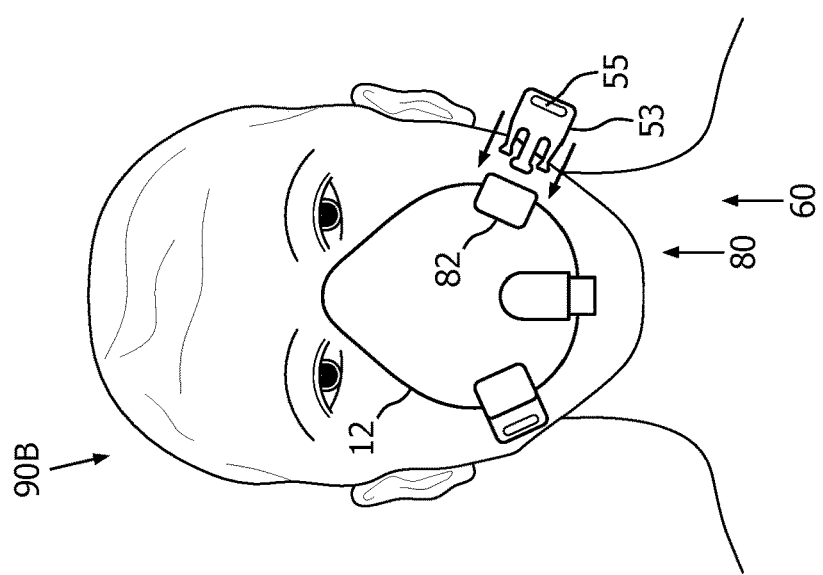
FIG. 3 is a schematic front view of a respiratory interface device with back-pack clips.

As used herein, the singular form of "a," "an," and "the" include plural references unless the context clearly dictates otherwise. As used herein, a "coupling" or "coupling component(s)" is one or more component(s) of a coupling assembly. That is, a coupling assembly includes at least two components that are structured to be coupled together. It is understood that the components of a coupling assembly are compatible with each other. For example, in a coupling assembly, if one coupling component is a snap socket, the other coupling component is a snap plug, or, if one coupling component is a bolt, then the other coupling component is a nut. It is further understood that an opening or passage through which another coupling component extends is also a coupling component.

As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other. Accordingly, when two elements are coupled, all portions of those elements are coupled. A description, however, of a specific portion of a first element being coupled to a second element, e.g., an axle first end being coupled to a first wheel, means that the specific portion of the first element is disposed closer to the second element than the other portions thereof. Further, a first object resting on a second object, which is held in place only by gravity, is not "coupled" to the second object unless the first object is otherwise linked to the second object. That is, for example, a book on a table is not coupled thereto, but a book glued to a table is coupled thereto.

As used herein, the term "number" shall mean one or an integer greater than one (i.e., a plurality). As used herein, "associated" means that the elements are part of the same assembly and/or operate together, or, act upon/with each other in some manner. For example, an automobile has four tires and four hub caps. While all the elements are coupled as part of the automobile, it is understood that each hubcap is "associated" with a specific tire.

As used herein, "correspond" indicates that two structural components are sized and shaped to be similar to each other and may be coupled with a minimum amount of friction. Thus, an opening which "corresponds" to a member is sized slightly larger than the member so that the member may pass through the opening with a minimum amount of friction. This definition is modified if the two components are said to fit "snugly" together or "snuggly correspond." In that situation, the difference between the size of the components is even smaller whereby the amount of friction increases. If the element defining the opening and/or the component inserted into the opening are made from a deformable or compressible material, the opening may even be slightly smaller than the component being inserted into the opening. This definition is further modified if the two components are said to "substantially correspond." "Substantially correspond" means that the size of the opening is very close to the size of the element inserted therein; that is, not so close as to cause substantial friction, as with a snug fit, but with more contact and friction than a "corresponding fit," i.e., a "slightly larger" fit. Further, as used herein, "loosely correspond" means that a slot or opening is sized to be larger than an element disposed therein. This means that the increased size of the slot or opening is intentional and is more than a manufacturing tolerance. Further, with regard to a surface formed by two or more elements, a "corresponding" shape means that surface features, e.g., curvature and contours, are similar.

As used herein, "structured to [verb] or 'be an [X]'" means that the identified element or assembly has a structure that is shaped, sized, disposed, coupled and/or configured to perform the identified verb or to be what is identified in the infinitive phrase. For example, a member that is "structured to move" is movably coupled to another element and includes elements that cause the member to move or the member is otherwise configured to move in response to other elements or assemblies. As such, as used herein, "structured to [verb] or 'be an [X]'" recites structure and not function. Further, as used herein, "structured to [verb] or 'be an [X]'" means that the identified element or assembly is intended to, and is designed to, perform the identified verb or to be an [X]. Thus, an element that is only possibly "capable" of performing the identified verb but which is not intended to, and is not designed to, perform the identified verb is not "structured to [verb] or 'be an [X]'."

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 20:
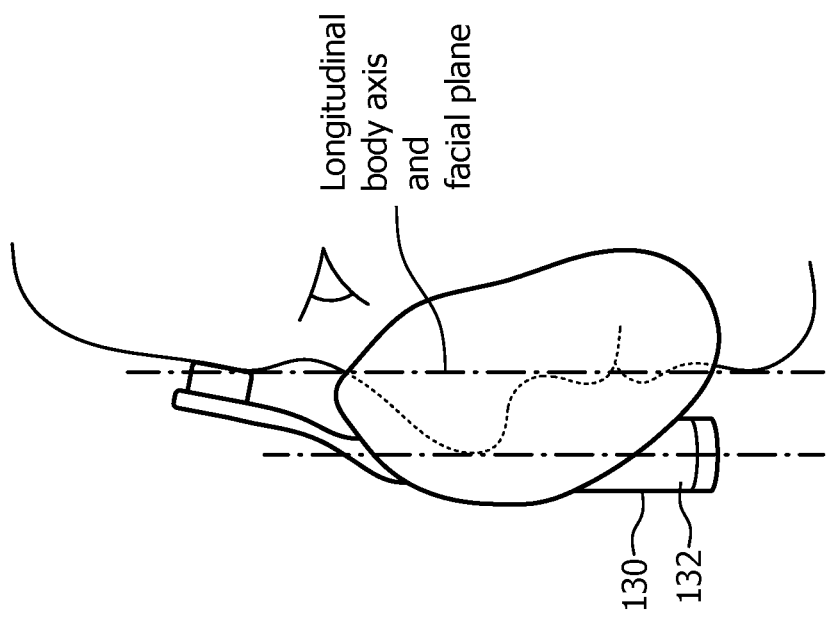
FIG. 20 is a side view of a custom fluid coupling wherein a user does not have a protruding chin and/or a recessed nose apex.

As used herein, a "respiratory interface device contour" is the perimeter of the area on a user's face that a respiratory interface device contacts. For a nasal and oral respiratory interface device, the "respiratory interface device contour" is a loop 1 that extends around the user's nose and mouth, as shown in FIG. 1. As used herein, a user's "longitudinal body axis" is a line extending generally parallel to the user's spine. That is, when a user is standing up, the "longitudinal body axis" is generally vertical and, when the user is lying on a bed, the "longitudinal body axis" is generally horizontal. As used herein, a user's "facial plane" is the plane defined by the user's nose apex and chin, at the greatest protuberance thereof. For users with a recessed nose apex and/or a non-protruding chin, the "longitudinal body axis" and the "facial plane" are generally parallel, as shown in FIG. 20. Conversely, for users with a protruding chin, the "longitudinal body axis" and the "facial plane" are angled relative to each other, as shown in FIG. 15. Further, as used herein, the upper portion of the user's nose, i.e., generally between the user's eyes, is the "apex" of the nose. The contour of the "apex," or "apex contour" as used herein, is the contour of the user's nose on both sides of the nose from the apex to a medial area of the nose.

As used herein, "generic" means as mass produced, i.e., as multiple components, units, devices, etc. that are substantially similar. As used herein, "custom" means a construct structured for use by a specific person or user. There may be a number of such constructs made, but the number does not rise to the level of "mass" production.

As used herein, a "custom feature" is a faceplate construct structured for use in association with a specific person's face. A "custom feature" includes a number of "selectable characteristics" or "custom characteristics" selected by the user. As used herein, "selectable characteristics" or "custom characteristics" include, but not limited to, a location characteristic, a type characteristic, a number characteristic, a contour characteristic, an orientation characteristic, and a visibility characteristic. Other "selectable characteristics" are identified below.

It is noted that, unless stated otherwise, for any given custom feature the "selectable characteristics" are selected from the group including or consisting of the "selectable characteristics" associated with that custom feature. The location for a "custom feature," as used herein, is not based on the optimal location for each individual, taking into account irregularities of the face. That is, the invention disclosed by WO 2014/075797 is specifically excluded from the definition of "custom feature" and "custom characteristic." The location of a "custom feature," i.e., the "location characteristic" of a "custom feature," is determined according to the user's preference, i.e., the user's choice and is not an optimal location. Further, any feature characteristics that are affected by a user's choice are also "custom characteristics." That is, if a user selects a certain feature characteristic (thereby making that characteristic a "custom characteristic") and other feature characteristics are altered, e.g., by a computer program structured to adjust or enhance such feature characteristics, the altered feature characteristics are also "custom characteristics" because such custom characteristics are affected by a user's choice.

As used herein, and in reference to a faceplate, "medial" means spaced from the faceplate peripheral end. Thus, a "medial" feature may be disposed outside, inside and/or through the faceplate so long as it is spaced from the faceplate peripheral end. Further, as used herein, a "medial feature" or a "medial custom feature" does not "directly affect" the shape or contour of the cushion coupled to the faceplate. As used herein, "directly affect" when used in reference to the relationship between the cushion and the faceplate means that the faceplate peripheral end contour deforms the cushion in a selected manner.

As used herein, "3D printing" means any fabrication method using a 3D printer or a similar device. "3D printing" also includes stereolithography, selective laser sintering and similar additive manufacturing techniques.

FIG. 1 shows a respiratory interface assembly 8 according to an embodiment of the invention. Respiratory interface assembly 8 includes a respiratory interface device 10 and a support assembly 50 such as, but not limited to a number of straps 54. Respiratory interface device 10 is shown as a nasal/oral respiratory interface device 10. It is understood, however, that respiratory interface device 10 can include, without limitation, a nasal mask, nasal pillows, or any other device that provides a suitable gas flow communicating function. Thus, as used herein, the term "respiratory interface device" shall refer to any of such devices. Respiratory interface device 10 is coupled to a pressure generating system 7 via a patient circuit 9, as is conventionally known in the art. For purposes of the present invention, the pressure generating system 7 is any device capable of generating a flow of breathing gas or providing gas at an elevated pressure. Examples of such pressure generating systems include a ventilator, CPAP device, or variable pressure device, e.g., an auto-titrating device, proportional assist ventilation (PAV®) device, proportional positive airway pressure (PPAP) device, C-Flex™ device, Bi-Flex® device, or a BiPAP® device manufactured and distributed by Philips Respironics of Murrysville, Pa., in which the pressure provided to the patient varies with the patient's respiratory cycle so that a higher pressure is delivered during inspiration than during expiration, or other pressure support device.

Respiratory interface device 10 includes a faceplate 12, a cushion 30, and a number of custom features 60, as discussed below. In an exemplary embodiment, faceplate 12 is a substantially rigid, convex body 14 structured to be disposed over, i.e., covering, a user's nose and mouth. This shape defines an interior space that accommodates a user's nose and other features when respiratory interface device 10 is in use. Faceplate 12 includes a peripheral end 18 that extends about faceplate 12. In this exemplary embodiment, faceplate peripheral end 18 extends generally towards the user's face when respiratory interface device 10 is in use. Faceplate peripheral end 18 includes an outer side 20, an inner side 22 (relative to the interior space), and a face side 24. That is, as used herein and with reference to faceplate 12, "outer" or "outwardly" means away from the interior space defined by bowl-shaped faceplate 12, and, "inner" or "inwardly" means toward the interior space defined by bowl-shaped faceplate 12. As is known, the faceplate 12 can be custom made to generally correspond to the user's respiratory interface device contour 1A. That is, the user's face is measured, e.g., scanned, and relevant dimensions are recorded, as discussed below. In an exemplary embodiment, the general shape of faceplate 12, faceplate peripheral end 18, and faceplate peripheral end face side 24 generally correspond to the user's respiratory interface device contour loop 1. Faceplate peripheral end 18 also defines a cushion coupling component 26. In an exemplary embodiment, faceplate cushion coupling component 26 is a tongue 28 structured to be coupled to a groove 40 in the cushion 30, as discussed below.

Faceplate 12, i.e., faceplate body 14, further includes a medial portion 16, a transition portion 17 and a peripheral end 18. As used herein, and in an exemplary embodiment, faceplate transition portion 17 is disposed between faceplate medial portion 16 and faceplate peripheral end 18. Further, as used herein, faceplate transition portion 17 is directly coupled to cushion 30 and directly affects cushion 30, as discussed below.

Figures 5, 6, 7:
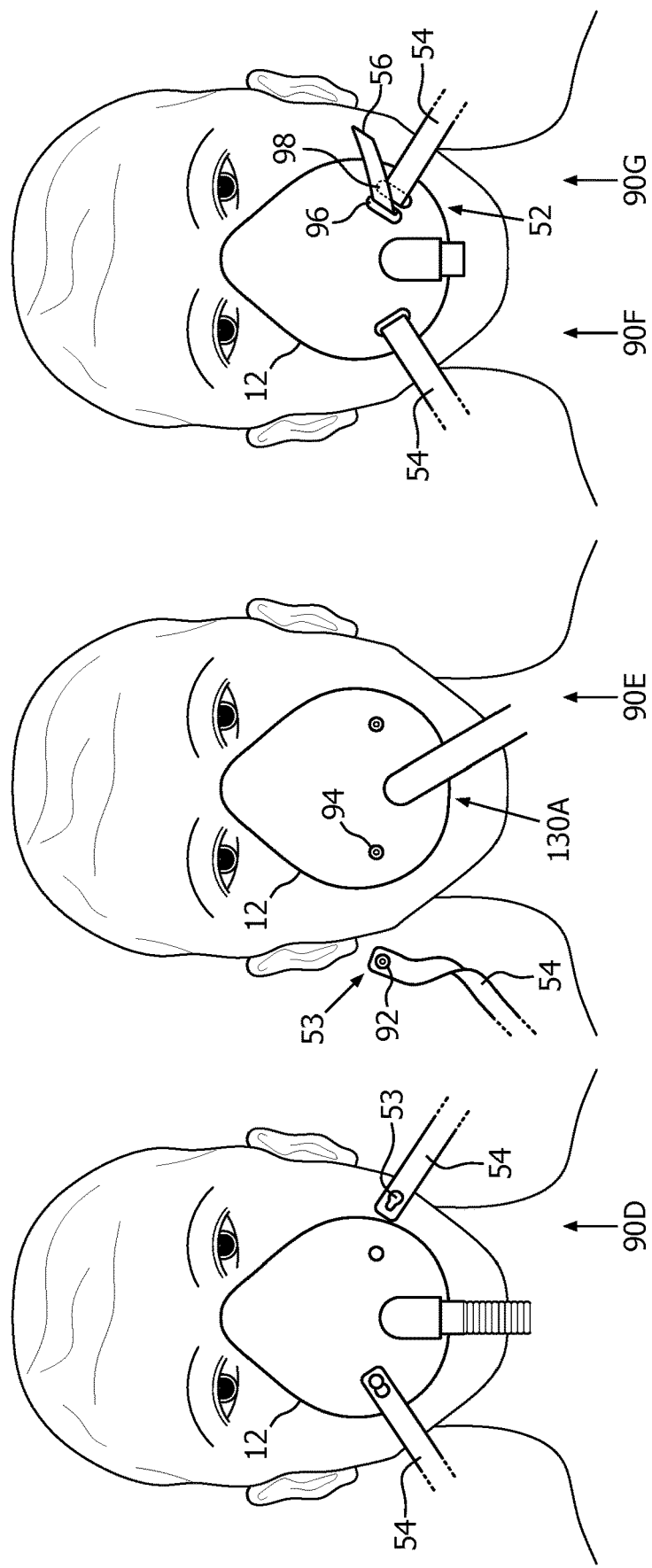
FIG. 5 is a schematic front view of a respiratory interface device with keyed-slot clips.
FIG. 6 is a schematic front view of a respiratory interface device with snaps.
FIG. 7 is a schematic front view of a respiratory interface device with slots.
Figure 8:
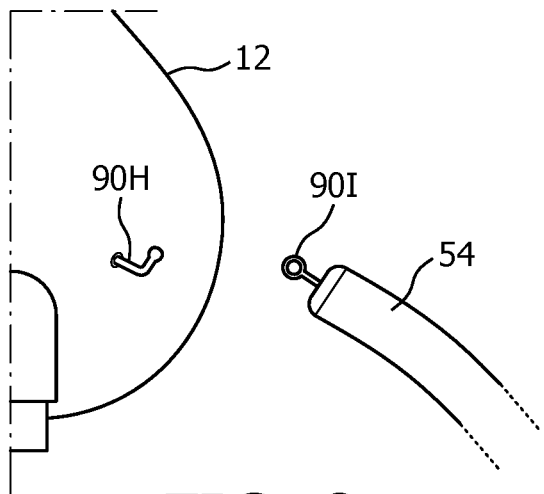
FIG. 8 is a schematic isometric view of a post and loop mechanical coupling.
Figure 9:
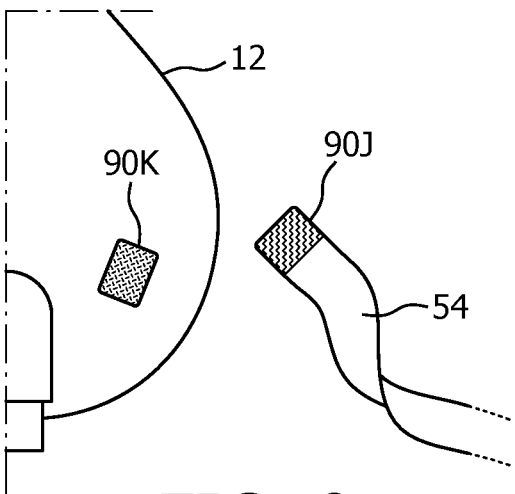
FIG. 9 is a schematic isometric view of a hook and loop mechanical coupling.
Figure 10:
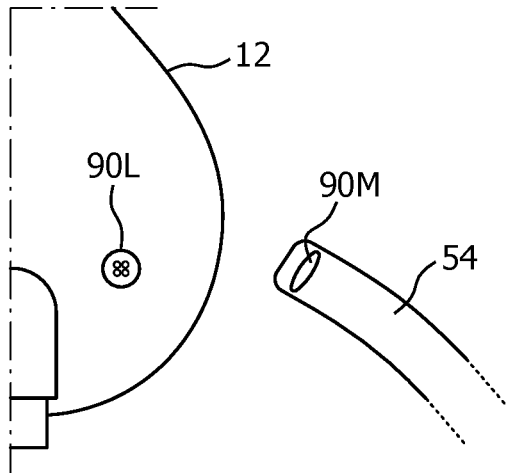
FIG. 10 is a schematic isometric view of a button and slot mechanical coupling.
Figure 11:
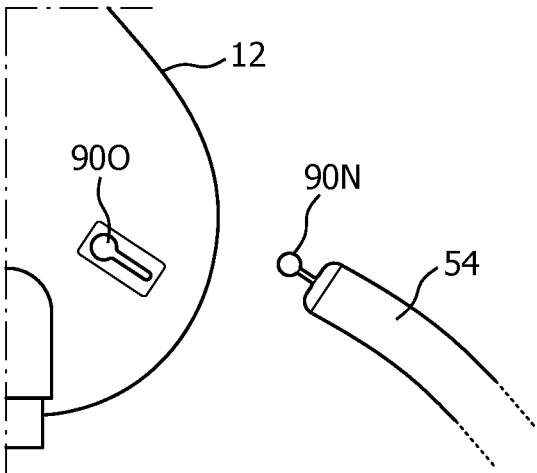
FIG. 11 is a schematic isometric view of a ball and socket mechanical coupling.
Figure 12:
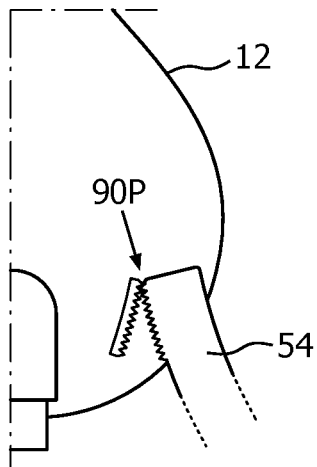
FIG. 12 is a schematic isometric view of a zipper mechanical coupling.

Respiratory interface device cushion 30 (hereinafter "cushion" 30) includes a body 32. Cushion body 32 can be constructed of a wide variety of resilient materials known in the art and can include, but is not limited to, a thermoplastic or thermoelastic material, including but not limited to an elastomer such as plastic, rubber, silicone, vinyl, foam, or any combination thereof. Cushion body 32 includes a coupling component 34 and an engagement portion 36. In the exemplary embodiment shown in FIG. 6, cushion body coupling component 34 is groove 40 within cushion body 32 that is structured to be coupled to tongue 28, as discussed above. Cushion engagement portion 36 is that portion of cushion body 32 that is directly coupled to the user's face. Cushion engagement portion 36 is shaped to generally follow user's respiratory interface device contour loop 1.

Cushion 30 is coupled, directly coupled, or removably coupled to faceplate body 14 adjacent faceplate peripheral end 18, e.g., by coupling faceplate cushion coupling component 26 to cushion body coupling component 34. In this configuration, faceplate peripheral end 18 directly affects the shape of cushion 30 and cushion engagement portion 36.

In an exemplary embodiment, support assembly 50 includes a number of coupling components 52 and a number of straps 54, shown schematically. Support assembly coupling components 52 are also part of the custom support assembly mechanical couplings 80 and are discussed below. Straps 54 may be elastic, inelastic, or a combination of both. Straps 54 may include an adjustment assembly structured to adjust the relative length of straps 54, i.e., the length of straps 54 relative to each other.

The problems identified above are solved by a number of custom features 60. In an exemplary embodiment, custom features 60 are disposed on faceplate medial portion 16 and may also be identified as "medial custom features." As discussed below, custom features 60 are selected by the user following a 3D scan of the user's face. Each custom feature 60 includes a number of selectable characteristics. A number of custom features 60 are identified below; the number of selectable characteristics associated with each custom feature 60 is also discussed. That is, in an exemplary embodiment, custom features 60 are selected from the group including, and/or consisting of, custom coupling assemblies 70 (shown in FIGS. 2-16), apertures 200, entrainment valves 136, and decorative elements 220.

Figure 2:
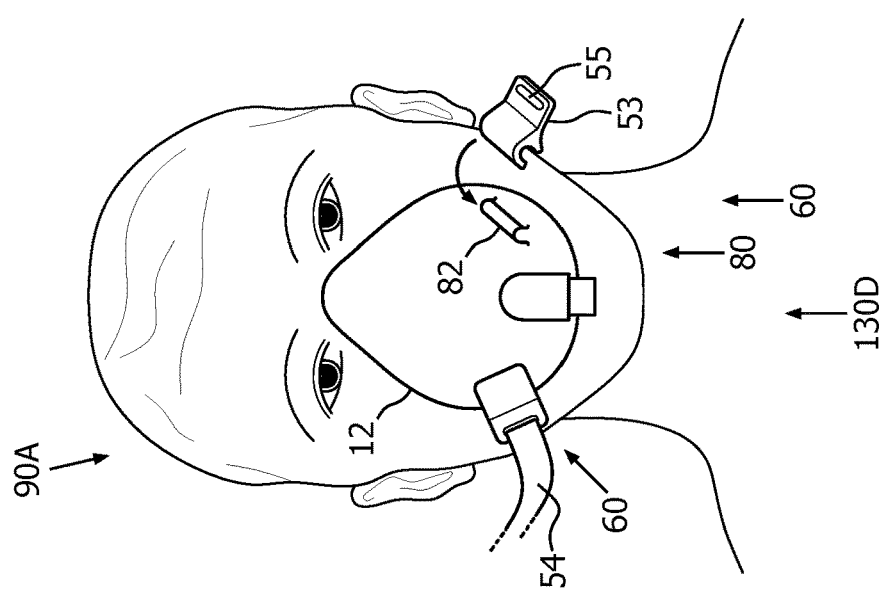
FIG. 2 is a schematic front view of a respiratory interface device with talon clips.

Custom coupling assemblies 70 are selected from the group including, and/or consisting of, custom support assembly mechanical couplings 80 (FIGS. 2-10), custom fluid couplings 120, electrical couplings 140, optical couplings 150, sensor couplings 160, and filter couplings 170. Each custom support assembly mechanical coupling 80 includes a number of coupling components including at least a faceplate coupling component 82 and support assembly coupling components 52. It is understood that support assembly coupling components 52 and faceplate coupling components 82 are compatible with each other. Generally, each faceplate coupling component 82 is coupled, directly coupled, fixed, or unitary with faceplate 12, and in an exemplary embodiment, faceplate medial portion 16. Each support assembly coupling component 52 is structured to be coupled or removably coupled to faceplate coupling component 82. Each support assembly coupling component 52 also includes a strap mount 53 (which is also a coupling component), such as, but not limited to a slot 55 (FIG. 2). Alternatively, in an embodiment wherein faceplate coupling component 82 includes a slot, e.g., slot 96, 98 (FIG. 7) discussed below, then a distal end 56 of strap 54 is support assembly coupling component 52.

Figure 13:
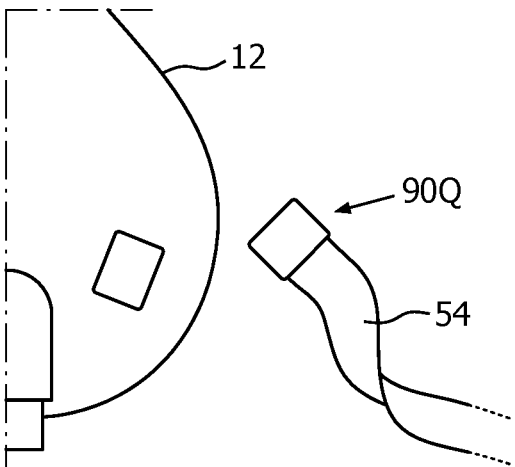
FIG. 13 is a schematic isometric view of an electro-adhesive pad mechanical coupling.

Custom support assembly mechanical couplings 80 include the following user selectable characteristics: a type characteristic, a location characteristic, an orientation characteristic, a number characteristic, a contour characteristic, a size characteristic and a "visibility characteristic." As used herein, and in reference to custom support assembly mechanical couplings 80, a "type characteristic" means the sort of coupling. In an exemplary embodiment, the user selects a type of custom support assembly mechanical coupling 80, e.g., from the types shown in FIGS. 2-7. For example, the custom support assembly couplings type characteristic is selected from the group including, and/or consisting of, talon clips 90A (FIG. 2), back-pack clips 90B (FIG. 3), magnetic clips 90C (FIG. 4), keyed-slot clips 90D (FIG. 5), snaps (i.e., plug-and-socket) 90E (FIG. 6), slots (through which strap 54 or loop is inserted) 90F (FIG. 7), double slots 90G (FIG. 7), post 90H and loop 90I (FIG. 8), hook 90J and loop 90K (FIG. 9), button 90L and slot 90M (FIG. 10), ball 90N and socket 90O (FIG. 11), zipper 90P (FIG. 12), and electro-adhesive pad 90Q (FIG. 13).

Unless used as an example below, a specific identification of each sort of faceplate coupling component 82 and each sort of support assembly coupling component 52 will not be set forth because such couplings are known to those of skill in the art. It is understood that components of each custom support assembly mechanical coupling 80 are reversible. That is, for example, snap 90E includes a plug 92 and a socket 94. In the embodiment shown, socket 94 is disposed on faceplate 12 and plug 92 is disposed on strap 54. It is understood that plug 92 could be disposed on faceplate 12 and socket 94 could be disposed on strap 54. This is generally true of any identified coupling assembly other than the slots 90F, 90G. That is, the location of the coupling components in custom support assembly mechanical couplings 80 are generally reversible.

Figure 14A:
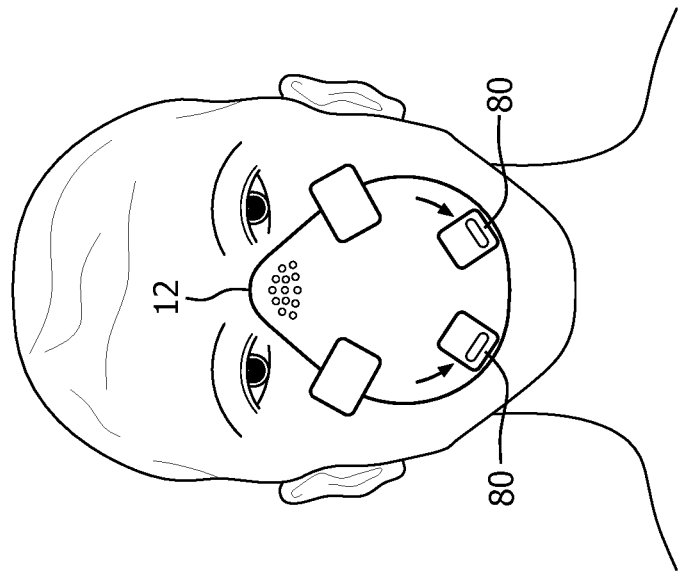
FIG. 14A is a schematic front view of a respiratory interface device with support assembly couplings in default locations.
Figure 14B:
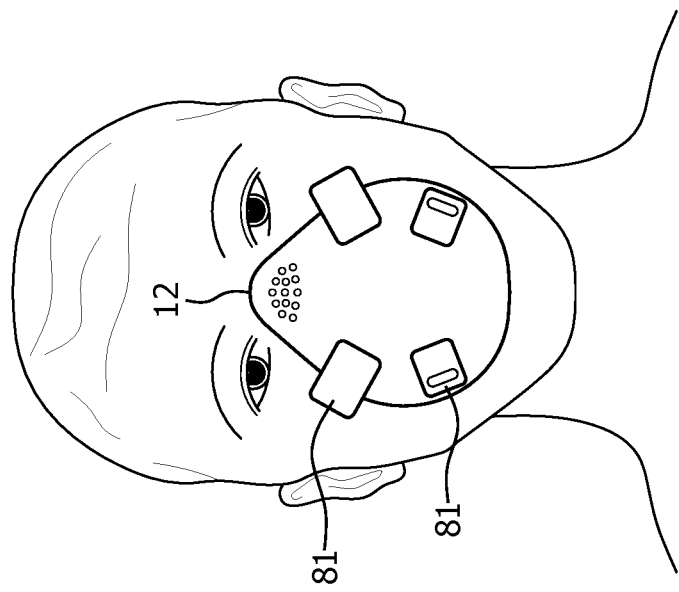
FIG. 14B is a schematic front view of a respiratory interface device with custom support assembly mechanical couplings in user selected locations.

As used herein, and in reference to custom support assembly mechanical couplings 80, a "location characteristic" means the location(s) on faceplate 12, and in an exemplary embodiment on faceplate medial portion 16, where custom support assembly mechanical couplings 80 are disposed. For example, in FIG. 14A, faceplate 12 includes default support assembly couplings 81 (default characteristics are discussed below). As shown in FIG. 14B, and as indicated by the arrows, the user has selected a new custom location for custom support assembly mechanical couplings 80. In another exemplary embodiment, shown in FIGS. 1, 15A and 15B, respiratory interface device 10 includes a forehead pad 15. As used herein, and in reference to custom support assembly mechanical couplings 80, the "location characteristic" includes locations on forehead pad 15.

As used herein, and in reference to custom support assembly mechanical couplings 80, an "orientation characteristic" means a construct that controls the direction of the longitudinal axis of strap 54. That is, one "orientation characteristic," as used herein, is a "multiple orientation characteristic" wherein the user selects the orientation of a strap relative to each custom support assembly mechanical coupling 80 and/or wherein the structure of support assembly 50 determines the "orientation characteristic" of strap 54. That is, for example, snap 90E (FIG. 6) is a multiple "orientation characteristic" because the user may twist plug 92 in socket 94 so that a strap may extend in a number of selected orientations. Alternatively, the structure of support assembly 50 may alter the orientation of strap 54 once the user couples plug 92 in socket 94 and releases strap 54. Conversely, in double slots 90G (FIG. 7) coupling there is a first slot 96 and a second slot 98. First and second slots 96, 98 each have a longitudinal axis which, in an exemplary embodiment, are generally parallel. When strap 54 is coupled to slots 96, 98 the longitudinal axis of strap 54 extends generally perpendicular to the longitudinal axes of slots 96, 98. Thus, by selecting the orientation of slots 96, 98, the user selects the resulting orientation of strap 54 coupled thereto.

Figure 15B:
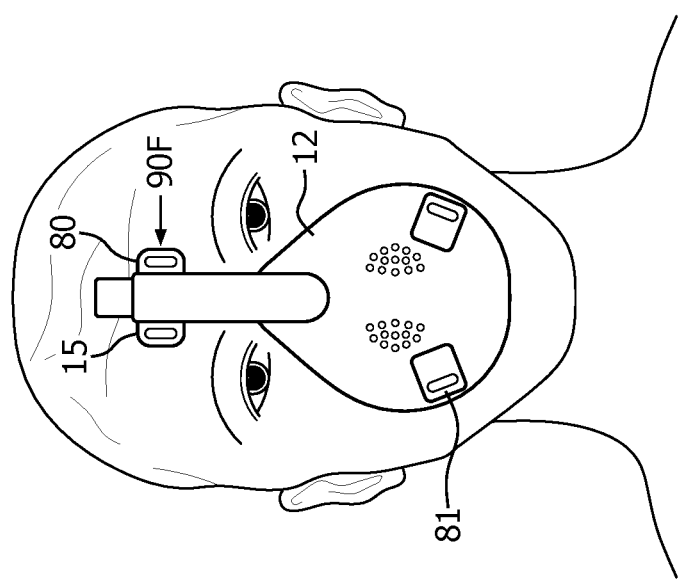
FIG. 15B is a schematic front view of a respiratory interface device with additional custom support assembly mechanical couplings.
Figure 15A:
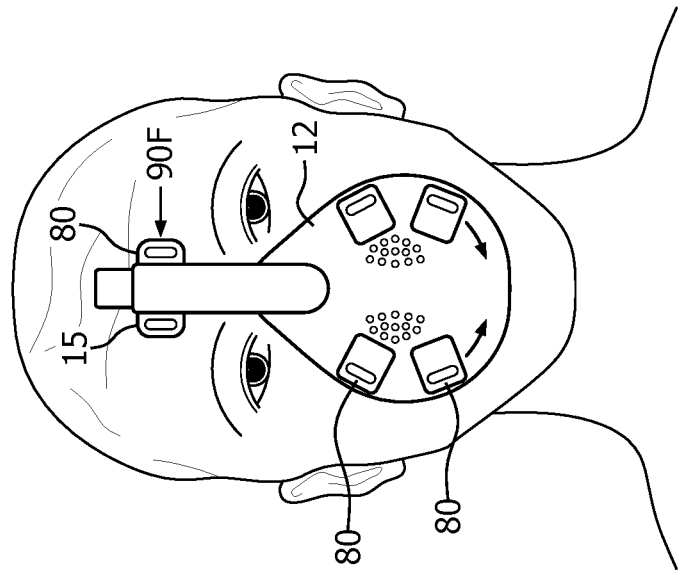
FIG. 15A is a schematic front view of a respiratory interface device with a default number of support assembly couplings in default locations.

As used herein, and in reference to custom support assembly mechanical couplings 80, a "number characteristic" means the number of custom support assembly mechanical couplings 80. It is understood that the number of faceplate coupling components 82 and the number of support assembly coupling components 52 are, in an exemplary embodiment, the same. That is, if the number characteristic of custom support assembly mechanical couplings 80 is two, then there are also two compatible faceplate coupling components 82 and support assembly coupling components 52. Thus, as shown in FIG. 15A, faceplate 12 includes a default number of two support assembly couplings 81. That is, the number characteristic is two. As shown in FIG. 15B, a user has selected to add an additional two custom support assembly mechanical couplings 80 above the default support assembly couplings 81. Thus, the number characteristic is now four. Further, as discussed below, the location of default support assembly couplings 81 are adjusted downwardly as indicated by the arrows. Thus, former default support assembly couplings 81 are now custom support assembly mechanical couplings 80, as discussed below.

Figure 16:
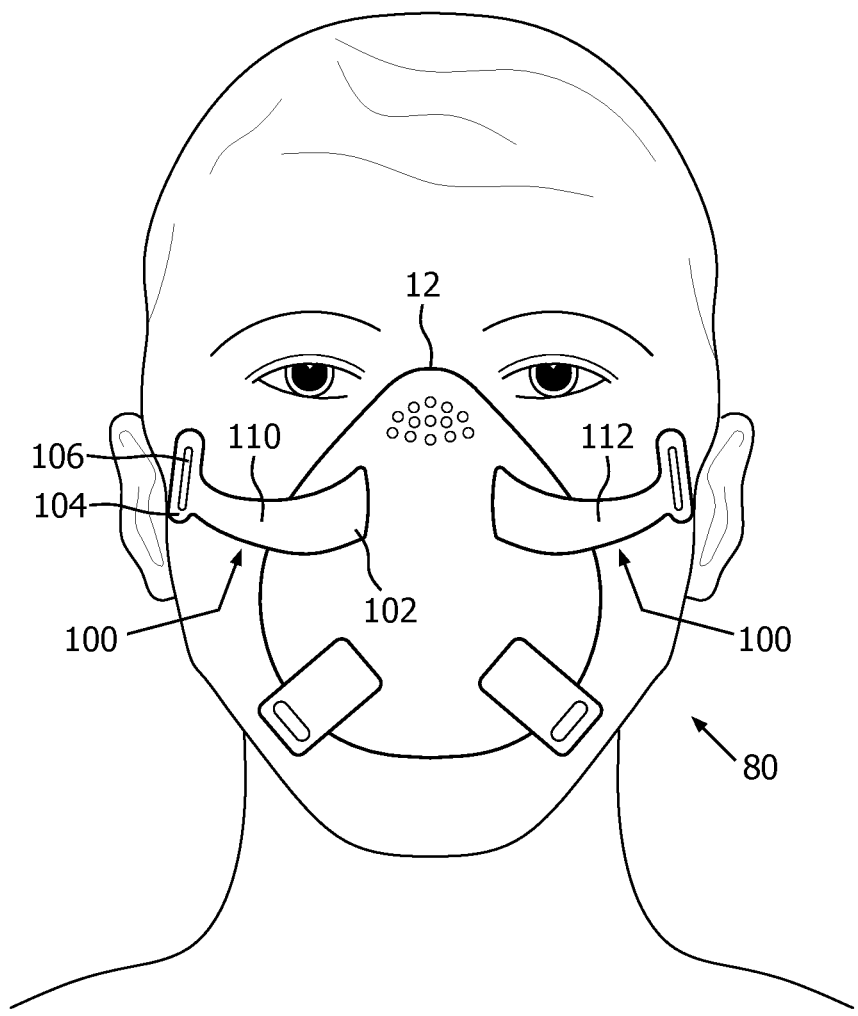
FIG. 16 is a schematic front view of a respiratory interface device with a contoured coupling component.

As used herein, and in reference to custom support assembly mechanical couplings 80, a "contour characteristic" means a custom shape of custom support assembly mechanical couplings 80. That is, custom support assembly mechanical couplings 80, in an exemplary embodiment, include a number of contoured coupling components 90. As shown in FIG. 16, and as used herein, a "contoured coupling component" is a support assembly coupling component 52 including a rigid body 100, hereinafter "contoured coupling component body 100," that is structured to correspond, i.e., be contoured to, a selected portion of a user's face. For example, a "contoured coupling component" structured to be disposed adjacent a user's eye, may be shaped to correspond to that user's cheek bones. As an alternative example, a "contoured coupling component" structured to be disposed adjacent a user's mouth, may be shaped to correspond to that user's jaw line. Contoured coupling component body 100 includes a first coupling component 102, structured to be coupled to faceplate coupling component 82, and a second coupling component 104, structured to be coupled to strap 54. Contoured coupling component body 100 is compatible with faceplate coupling component 82. Contoured coupling component body second coupling component 104 is, in an exemplary embodiment, a slot 106.

As used herein, and in reference to custom support assembly mechanical couplings 80, a "size characteristic" means the size of the custom support assembly mechanical coupling 80. For example, a custom support assembly mechanical coupling 80 is, in one exemplary embodiment, sized to be grasped by a user with normal dexterity and is, as used herein, "hand sized." That is, a "hand sized" custom support assembly mechanical coupling 80 is the size that one of skill in the art would make for an average sized user with normal dexterity. In another embodiment, a custom support assembly mechanical coupling 80 is sized to be grasped by a user with limited dexterity and is, as used herein, "over-sized." That is, an "over-sized" custom support assembly mechanical coupling 80 is larger than a "hand sized" custom support assembly mechanical coupling 80 and is the size that one of skill in the art would make for an average sized user with limited dexterity.

In an exemplary embodiment, wherein a user has a right facial feature and left facial feature, such as but not limited to right and left cheekbones, contoured coupling components 90 include a right contoured coupling component body 110 and a left contoured coupling component body 112. Right contoured coupling component body 110 is contoured to correspond to a specific user's right facial contour, and, left contoured coupling component body 112 is contoured to correspond to a specific user's left facial contour.

As used herein, and in reference to custom support assembly mechanical couplings 80, a "visibility characteristic" means the portion of the respiratory interface device 10 visible to the user at the apex of the user's nose. That is, as used herein, and in reference to custom support assembly mechanical couplings 80, the "visibility characteristic" only applies to respiratory interface device 10 including forehead pad 15. In an exemplary embodiment, respiratory interface device 10 includes a support 19 that extends between faceplate medial portion 16 and forehead pad 15. Support 19 extends over the apex of the user's nose. As used herein, and in reference to custom support assembly mechanical couplings 80, the "visibility characteristic" is one of "low visibility" wherein support 19 is disposed substantially in the far peripheral field of view, i.e., greater than a radius of about 60° (centered around the fixation point), "intermediate visibility" wherein support 19 is disposed substantially in the mid-peripheral field of view, i.e., between a radius of about 60° and 30°, or "high visibility" wherein support 19 is disposed substantially in the near-peripheral field of view, i.e., less than a radius of about 30°. Further, in an exemplary embodiment, the contour of support 19 rear surface 21, i.e., the surface of support 19 adjacent the user's face, corresponds to the user's apex contour.

In an exemplary embodiment, there is a single custom fluid coupling 120. Custom fluid coupling 120 includes a number of coupling components including a faceplate fluid coupling component 122 and pressure generating system component 7. Faceplate fluid coupling component 122, in an exemplary embodiment, includes an opening 124 in faceplate body 14 and an inlet element 126. Inlet element 126 is in fluid communication with pressure generating system 7 via pressure generating system component. Inlet element 126 is also in fluid communication with faceplate fluid coupling opening 124. Thus, a fluid is transferred from pressure generating system 7 to faceplate 12 interior space.

Figure 19B:
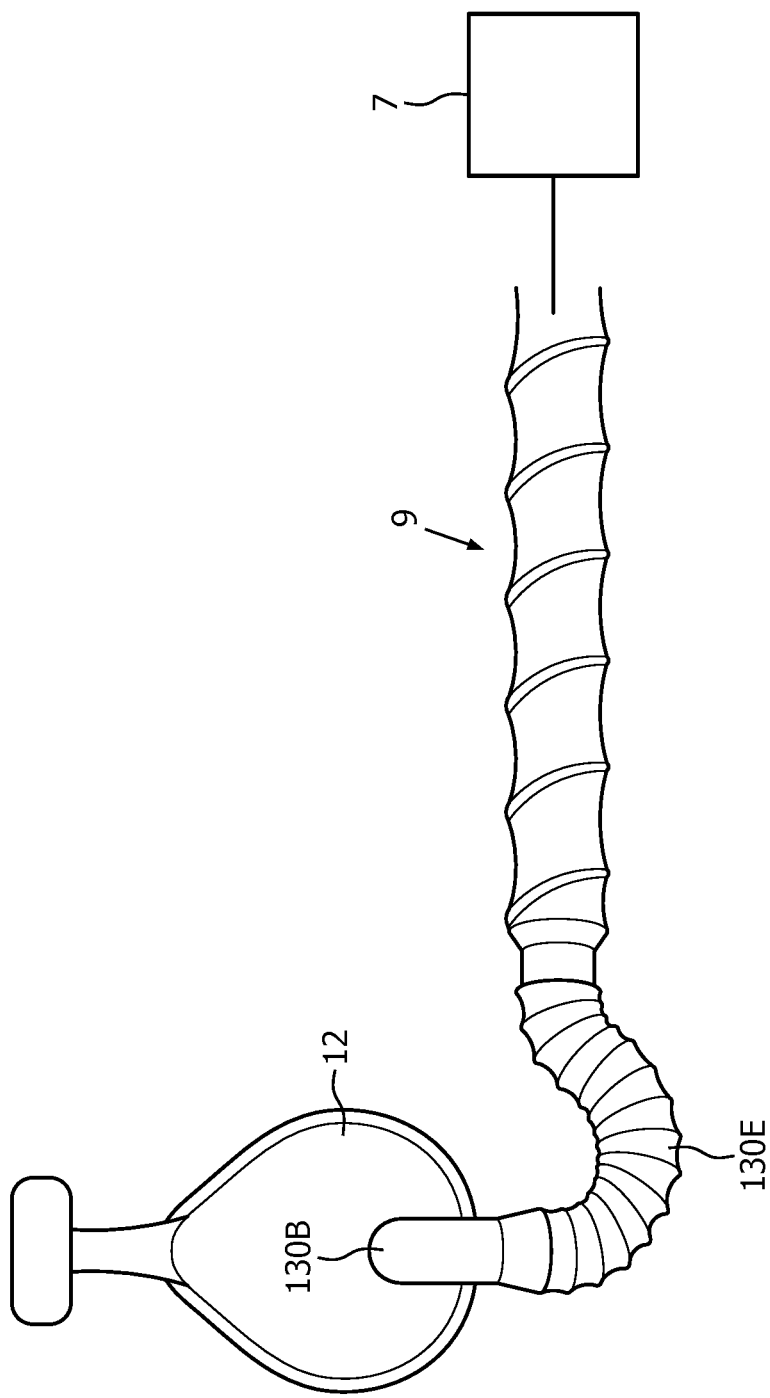
FIG. 19B is a schematic view of a flexible tube/pigtail hose fluid coupling.
Figure 19C:
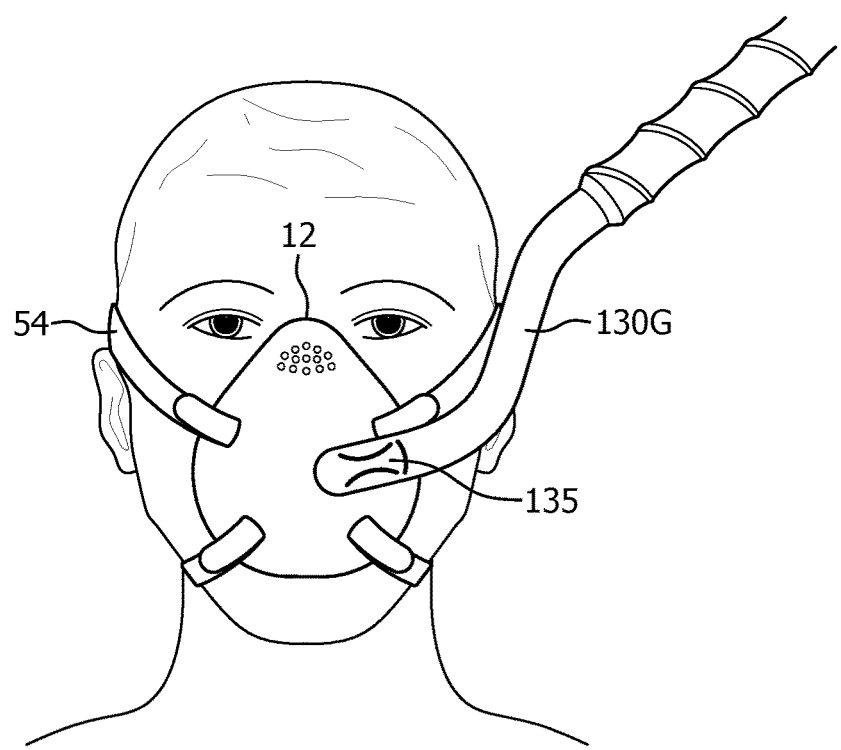
FIG. 19C is a schematic view of a single side tube, heated connector fluid coupling.
Figure 23A:
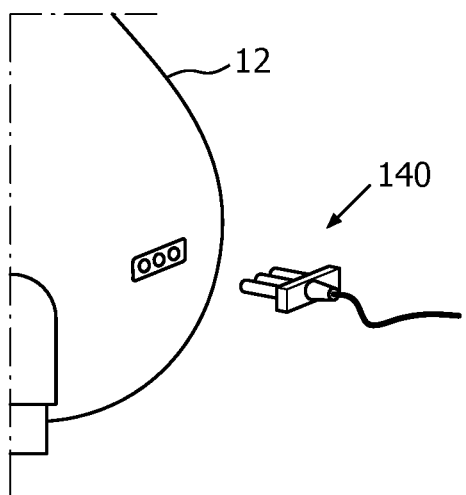
FIG. 23A is a schematic isometric view of a plug and socket electrical coupling.
Figure 23B:
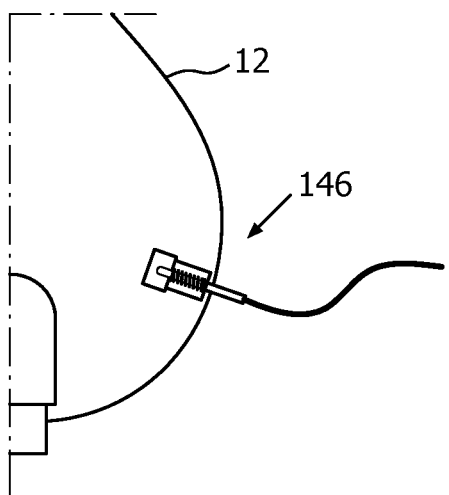
FIG. 23B is a schematic isometric view of a pogo pin electrical coupling.
Figure 23C:
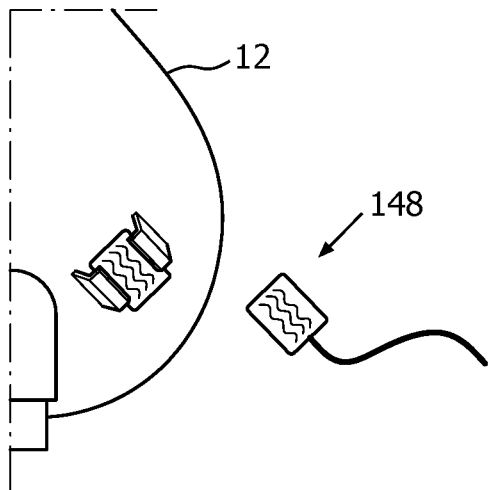
FIG. 23C is a schematic isometric view of an inductive electrical coupling.

Custom fluid coupling 120 includes the following user selectable characteristics: a type characteristic, a location characteristic, an orientation characteristic, and a visibility characteristic. As used herein, and in reference to custom fluid coupling 120, a "type characteristic" means the sort of coupling. In an exemplary embodiment, the custom fluid coupling 120 "type characteristic" is selected from the group including, and/or consisting of, generally straight rotatable couplings 130A (FIG. 6), pivotal elbow couplings 130B (FIG. 1), Tube-In-Headgear (TIHM) 130C (FIG. 19A), generally straight non-rotatable couplings 130D (FIG. 2), flexible tube/pigtail hose 130E (FIG. 19B), forehead-mounted tube 130F (FIG. 18), single side tube, heated connector 130G (FIG. 19C) including a heating assembly 135, an entrainment valve 136 (FIG. 19D-19F) and fluid coupling with integrated electrical connector (e.g., an inductive coupling, similar to FIG. 23C).

As is known, a rotatable coupling 130A includes an inlet element 126 that is a generally straight tube 132 rotatably coupled to faceplate opening. Pivotal elbow coupling 130B is similar, but with inlet element 126 that is an angled tube 134 rotatably coupled to faceplate opening. Tube-In-Headgear 130C includes passages (not shown) defined by support assembly 50. That is, in an exemplary embodiment, straps 54 define passages that are coupled to, and in fluid communication with, pressure generating system 7. Straps 54 defining passages are coupled to inlet element 126 such as a collar 138 (FIG. 19) disposed about, i.e., around, faceplate opening. In this embodiment, custom support assembly mechanical couplings 80 and custom fluid couplings 120 are coextensive.

As used herein, and in reference to custom fluid coupling 120, a "location characteristic" means the location(s) on faceplate 12, and in an exemplary embodiment on faceplate medial portion 16, where custom fluid coupling 120 is disposed. In an exemplary embodiment, the location characteristic for custom fluid coupling 120 is selected from the group including, and/or consisting of, a lower location (FIG. 17), an upper location (FIG. 18), and lateral locations (FIG. 19). As used herein, a "lower location" is generally centrally disposed on faceplate 12 and adjacent the user's mouth. As used herein, an "upper location" is generally centrally disposed on faceplate 12 and adjacent the user's nose and, in an exemplary embodiment, at the apex of the user's nose. As used herein, "lateral locations" are a pair of aligned openings disposed on either side of the user's nose.

Figure 21:
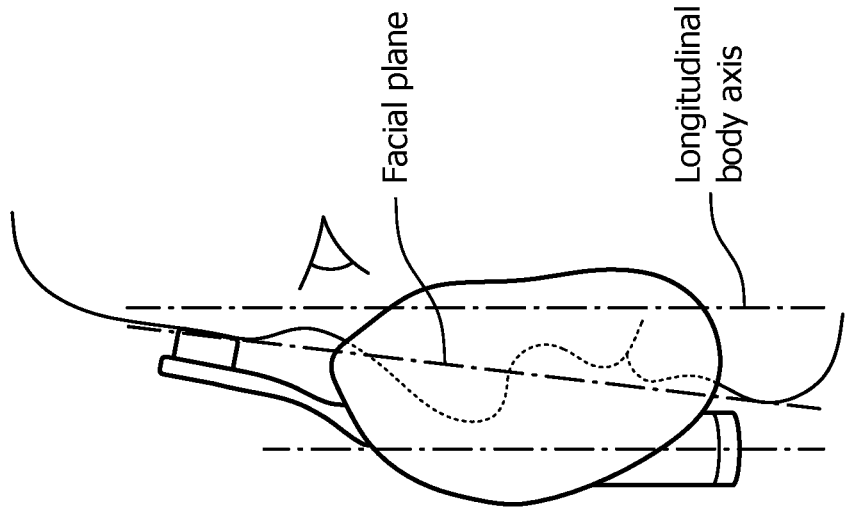
FIG. 21 is a side view of a custom fluid coupling wherein a user has a protruding chin and/or a recessed nose apex.

As used herein, as shown in FIGS. 20-21, and in reference to custom fluid coupling 120, an "orientation characteristic" means the direction of the longitudinal axis of inlet element 126. In an exemplary embodiment, inlet element 126 is generally circular and the longitudinal axis of inlet element 126 extends along the center of inlet element 126. It is noted that custom fluid coupling 120 orientation characteristic affects the orientation of pressure generating system patient circuit coupling (not shown) which, in an exemplary embodiment, includes a generally flexible, elongated tube (not shown). For example, certain users prefer that the pressure generating system tube extends generally parallel to the user's longitudinal body axis. For a user who does not have a protruding chin and/or a recessed nose apex, the facial plane and the longitudinal body axis are generally parallel and the longitudinal axis of inlet element 126, i.e., the "orientation characteristic" of custom fluid coupling 120 is generally parallel to both, as shown in FIG. 20. Conversely, for a user with a protruding chin, shown in FIG. 21, the facial plane and the longitudinal body axis are angled relative to each other and the longitudinal axis of inlet element 126, i.e., the "orientation characteristic" of custom fluid coupling 120 is at an angle of between about ninety degrees and zero degrees. In an exemplary embodiment, the "orientation characteristic" of custom fluid coupling 120 is zero degrees relative to the user's facial plane, i.e., parallel relative to the user's facial plane. In this configuration, a user with a protruding chin also has the longitudinal axis of inlet element 126 generally parallel to the user's longitudinal body axis.

Figure 22:
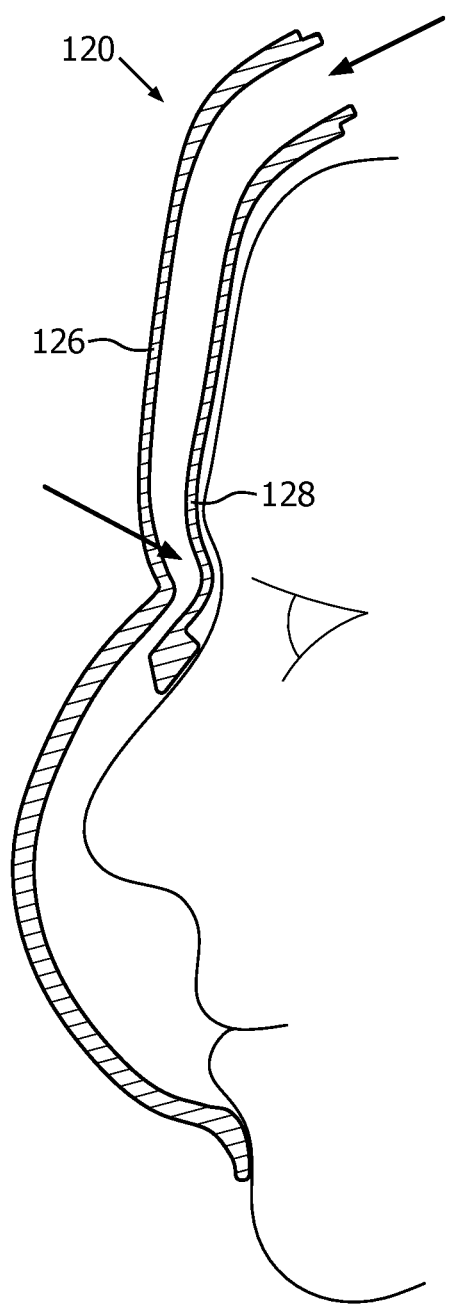
FIG. 22 is a side view of a custom fluid coupling that generally corresponds to a user's nose apex.

As used herein, and in reference to custom fluid coupling 120, a "visibility characteristic" means the portion of the respiratory interface device 10 visible to the user at the apex of the user's nose. That is, as shown in FIG. 22, custom fluid coupling 120 disposed at the upper location generally extends over the apex of the user's nose. In an exemplary embodiment, custom fluid coupling 120 disposed at the upper location is a 3D printed inlet element 126. Inlet element 126 includes a rear surface 128 that is disposed adjacent to the user's face. Further, as used herein, and in reference to custom fluid coupling 120, a "visibility characteristic" only applies to inlet element 126 extending over the apex of the user's nose. As used herein, and in reference to custom fluid coupling 120, the "visibility characteristic" is one of a "low visibility" element wherein inlet element 126 is disposed substantially in the far peripheral field of view, i.e., greater than a radius of about 60° (centered around the fixation point), an "intermediate visibility" element wherein inlet element 126 is disposed substantially in the mid-peripheral field of view, i.e., between a radius of about 60° and 30°, or a "high visibility" element wherein inlet element 126 is disposed substantially in the near-peripheral field of view, i.e., less than a radius of about 30°. Generally, an object in the far peripheral field of view, i.e., an object with a low visibility, visibility characteristic, is disposed in the user's "apex blind spot," as used herein. Further, in an exemplary embodiment, the contour of inlet element rear surface 128, i.e., the surface of inlet element 126 adjacent the user's face, generally corresponds to the user's apex contour.

Figure 19D:
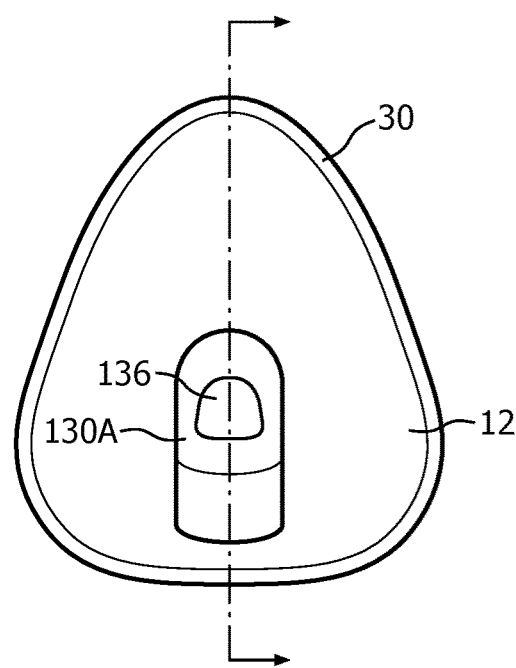
FIG. 19D is a schematic front view of an entrainment valve.
Figure 19E:
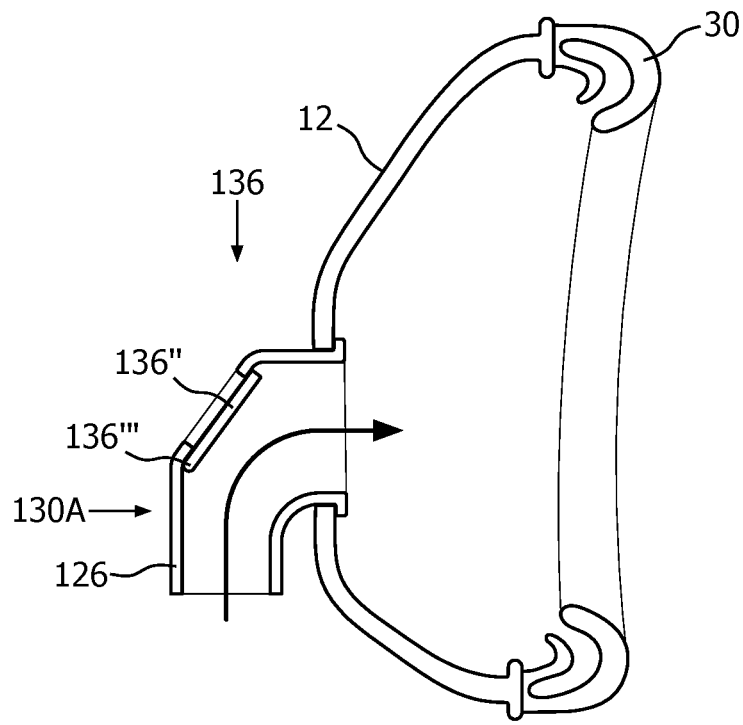
FIG. 19E is a schematic cross-sectional view of an entrainment valve in a first position.
Figure 19F:
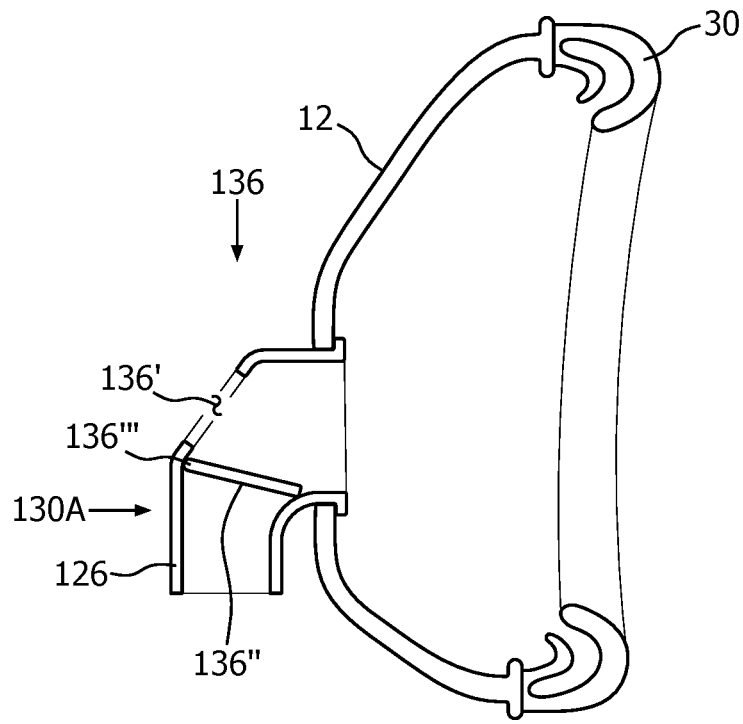
FIG. 19F is a schematic cross-sectional view of an entrainment valve in a second position.

In another exemplary embodiment, shown in FIGS. 19D-19F, rotatable coupling 130A includes an entrainment valve 136. Entrainment valve 136 is structured to selectively allow the user to draw incoming breathing gas from pressure generating system 7 or from the atmosphere. In an exemplary embodiment, entrainment valve 136 includes a passage 136' (FIG. 19F) through rotatable coupling 130A, a valve member 136" and a hinge 136''', such as, but not limited to, a living hinge. In an exemplary embodiment, valve member 136" and hinge 136''' are 3D printed elements. Hinge 136''' movably coupled valve member 136" to rotatable coupling 130A. Valve member 136" is structured to move between a closed, first position (FIG. 19E), wherein valve member 136" substantially seals passage 136' and whereby breathing gas from pressure generating system 7 is directed to respiratory interface device 10, and, an open, second position (FIG. 19F), wherein valve member 136" substantially seals inlet element 126 and whereby breathing gas from the atmosphere is directed to respiratory interface device 10.

Figure 23D:
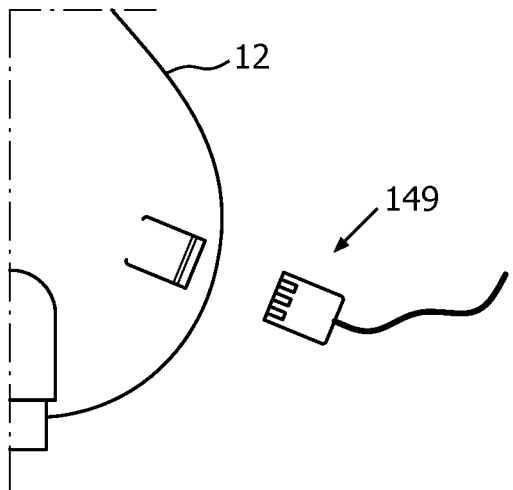
FIG. 23D is a schematic isometric view of a multi-conductor connector electrical coupling.

Electrical couplings 140 are structured to allow a current to pass from a component on the respiratory interface device 10 and/or the support assembly 50 to another assembly such as, but not limited to a computer or transmitter (neither shown). In addition to a "number characteristic," a "size characteristic" and a "location characteristic," as defined above, electrical couplings 140 include selectable characteristics selected from the group including or consisting of the following selectable characteristics: A "type characteristic," a "configuration characteristic," a "key characteristic," a "lock characteristic," an "attachment characteristic," a "power characteristic," a "transmission characteristic," and a "signal characteristic." As used herein, and in reference to electrical couplings 140, a "type characteristic" means the sort of electrical coupling 140. That is, for example, the "type characteristic" includes types of electrical couplings 140 selected from the group including, and/or consisting of, plug 142 and socket 144 (FIG. 23A), contact connector 146 (e.g., pogo pin) (FIG. 23B), an inductive coupling 148 including two inductive pads and a mounting bracket (FIG. 23C), or a multi-conductor connector 149 (FIG. 23D), such as, but not limited to a Universal Serial Bus (USB) connection.

Further, as used herein, and in reference to electrical couplings 140, a "configuration characteristic" relates to the pattern of the conductive members. As used herein, and in reference to electrical couplings 140, a "key characteristic" relates to an orientation device for the electrical coupling 140. That is, in reference to electrical couplings 140, the orientation device is structured to ensure the electrical coupling 140 components are fitted together in the proper orientation so that the conductive elements become electrically coupled with the proper opposing conductive elements. A key characteristic includes, but is not limited to a protrusion (or key) in the female connector and a corresponding cavity in the male connector. Other key characteristic may be a shaped housing, e.g., a trapezoidal housing on the male connector and housing on the female connector defining a trapezoidal cavity (neither shown).

As used herein, a "lock characteristic" means any type of locking assembly structured to maintain the connectors of an electrical coupling 140 in electrical communication. As used herein, an "attachment characteristic," means any type of mounting associated with electrical couplings 140 such as, but not limited to a housing on the male connector and a housing on the female connector which are not the conductive elements. As used herein, a "power characteristic," means that the electrical coupling is structured for use with a self-powered electrical component, i.e., powered by a battery, or remotely powered. Electrical coupling 140 for a remotely powered component includes power conductors and electrical coupling 140 for a self-powered electrical component does not include power conductors. As used herein, a "transmission characteristic," means that electrical coupling 140 is structured for wireless or wired communication. Electrical coupling 140 for a wireless component does not include a conductor for electronic communication of data. Conversely, electrical coupling 140 for a wired component includes a conductor for electronic communication of data. As use herein, a "signal characteristic" means that the signal used for electronic communication is either analog, digital, or a combination thereof.

Figure 24A:
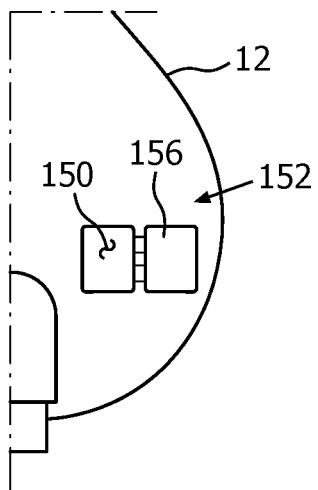
FIG. 24A is a schematic isometric view of a covered port optical coupling.
Figure 24B:
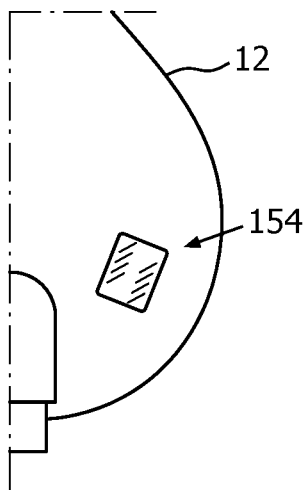
FIG. 24B is a schematic isometric view of a transparent port optical coupling.

Optical couplings 150 are structured to allow a person or device to view a portion of the respiratory interface device 10 during use. For optical couplings 150, the "type characteristic" means the sort of coupling and includes covered ports 152 (FIG. 24A) and transparent ports 154 (FIG. 24B). Covered port 152 is an opening in faceplate 12 that has an associated movable cover 156. Optical couplings 150 also have selectable characteristics selected from the group including or consisting of "number characteristics," and "location characteristics," as defined above.

Figure 25:
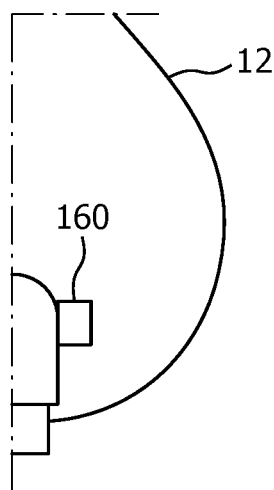
FIG. 25 is a schematic isometric view of a sensor coupling.

Sensor couplings 160 (FIG. 25) are structured to couple a sensor to the respiratory interface device 10 during use. For sensor couplings 160, the "type characteristic" means the sort of coupling and includes pressure port, chemical breath analysis (e.g., $O_2$, $CO_2$, or heart failure markers like acetone, pentane, nitric oxide), and heart rate monitor. Sensor couplings 160 also have selectable characteristics selected from the group including or consisting of "number characteristic," and "location characteristic," as defined above.

Figure 26A:
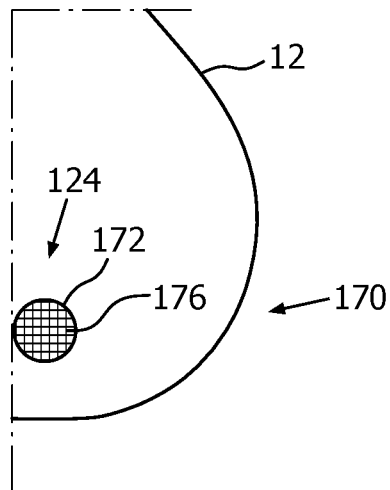
FIG. 26A is a schematic isometric view of an inhaled air filter coupling.
Figure 26B:
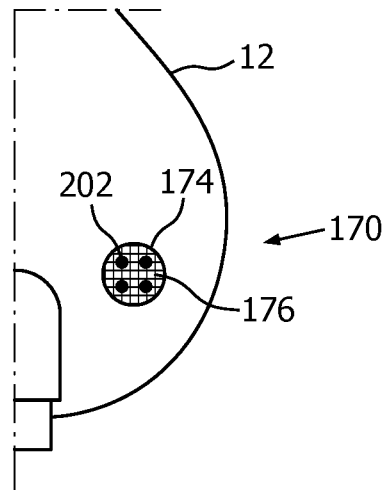
FIG. 26B is a schematic isometric view of an exhaled air filter coupling.

Filter couplings 170 are structured to couple a filter element 176 to the respiratory interface device 10 during use. For filter couplings 170, the "type characteristic," as used herein means the sort of coupling and includes an inhaled air filter coupling 172 (FIG. 26A) and an exhaled air filter coupling 174 (FIG. 26B) for a filter element 176. Filter element 176 may be a porous material, a woven material, a mesh material, or any other known filter material. Generally, inhaled air filter coupling 172 is associated with custom fluid coupling 120 and is disposed in faceplate fluid coupling component opening 124. As shown, and in an exemplary embodiment, inhaled air filter coupling 172 is a snap in coupling for a filter element 176. Exhaled air filter coupling 174 is structured to disposed filter element 176 over an exhaust such as apertures 200, discussed below. Filter couplings 170 also have selectable characteristics selected from the group including or consisting of "number characteristic," and "location characteristic," as defined above.

Figure 27A:
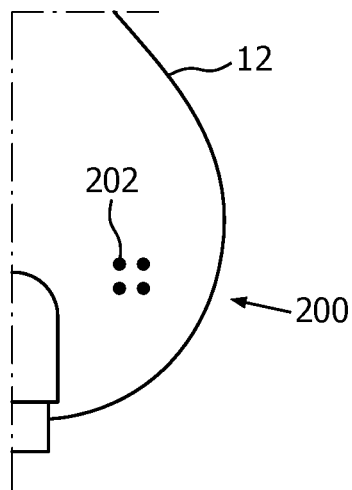
FIG. 27A is a schematic isometric view of an exhaust aperture.
Figure 27B:
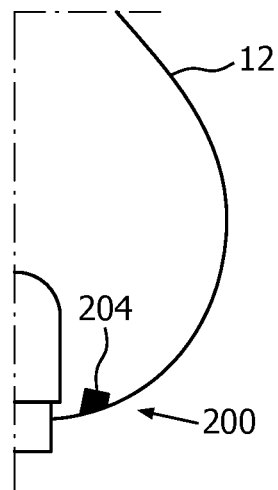
FIG. 27B is a schematic isometric view of a drain aperture.

Apertures 200 are passages through faceplate 12 through which no component passes. Aperture 200 "type characteristics," as used herein include, but are not limited to, exhaust apertures 202 (FIG. 27A) and drain aperture 204 (FIG. 27B).

In addition to a "number characteristic," and "location characteristic," as defined above, apertures 200 include selectable characteristics selected from the group including or consisting of the following: A "shape characteristic" which, as used herein, means the shape of an opening which may be, but is not limited to, generally circular, generally oval, and slots; an "area characteristic" which, as used herein, means the cross-sectional area of an opening; a "pattern characteristic" which, as used herein, means a defined pattern such as, a grid or matrix; or, a selected pattern shape, such as a plurality of small openings forming a pattern such as, but not limited to an oval. A "flow resistance characteristic" which, as used herein, defines airflow through aperture 200 at a given therapy pressure.

Entrainment valves 136 (FIG. 19D) are selected from the group comprising, or consisting of, including: anti-asphyxia valves, fresh air inlet valves, and plateau exhalation valves (PEV). In addition to selectable characteristics selected from the group including or consisting of "type characteristic," "number characteristic," and "location characteristic," as defined above, entrainment valves 136 include a "dimension characteristic" which, as used herein, means the size of the entrainment valves 136.

Figure 28:
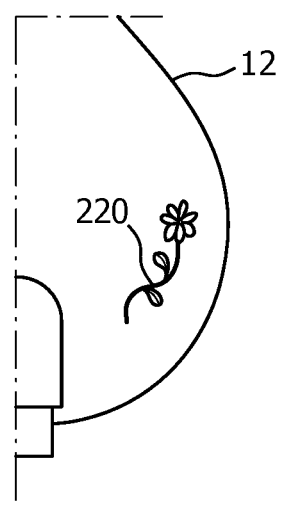
FIG. 28 is a schematic isometric view of a decorative element.

Decorative elements 220 (FIG. 28) include colored panels, logos/images, and trim structures. In addition to a "number characteristic," and "location characteristic," as defined above, decorative elements 220 include the following user selectable characteristics: contour characteristics and proportion characteristics. As used herein, a "contour characteristic" means the surface features of a design, such as, but not limited to, texture. As used herein, a "proportion characteristic" means the size of the decorative elements 220. For example, a decorative element 220, in an exemplary embodiment, a flower design, may be formed by contouring a flower pattern into faceplate 12. Further, the surface of the flower pattern may be colored so that, for example, a rose is red, a violet is blue and a stem is green.

Figure 29:
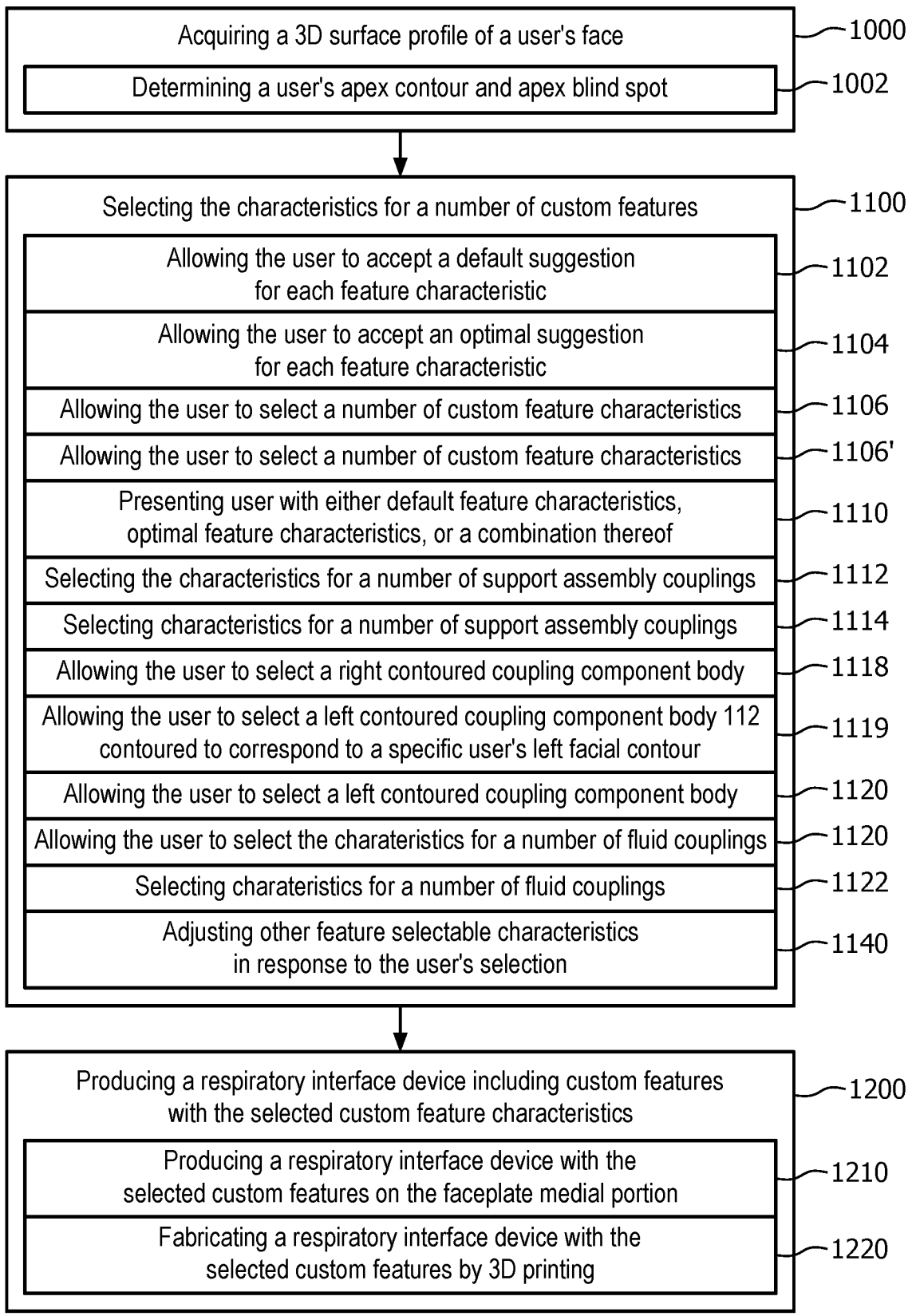
FIG. 29 is a flow chart of the disclosed method.

As shown in FIG. 29, a method of making respiratory interface device 10 including custom features 60 includes: acquiring 1000 a 3D surface profile of a user's face, selecting 1100 the characteristics for a number of custom features 60, and producing 1200 a respiratory interface device 10 including custom features 60 with the selected custom feature characteristics.

As is known, acquiring 1000 a 3D surface profile of a user's face is best accomplished by a 3D scanner coupled to a computer structured to store the image and to convert the image to data representing the 3D image (no system elements shown). Computer is, in an exemplary embodiment, structured to provide a default suggestion for each feature characteristic, hereinafter a "default feature characteristic." As used herein, a "default" suggestion is based on the type, sort, or model of respiratory interface device 10 and is independent of the user's 3D surface profile. As is known, the default suggestions are stored in a database module wherein each type, sort, or model of respiratory interface device 10 has an associated set of data representing the default suggestions. Further, computer is, in an exemplary embodiment, structured to provide an optimal suggestion for each feature characteristic, hereinafter a "optimal feature characteristic." As used herein, an "optimal feature characteristic" suggestion is based on the user's 3D surface profile. Acquiring 1000 a 3D surface profile of a user's face further includes determining 1002 a user's apex contour and apex blind spot. That is, the scan may acquire additional data in the area around the user's nose apex.

Selecting 1100 the characteristics for a number of custom features 60 includes allowing the user to accept 1102 a default suggestion for each feature characteristic, allowing the user to accept 1104 an optimal suggestion for each feature characteristic, and allowing the user to select 1106 a number of custom feature characteristics. That is, following the acquisition 1000 of a 3D surface profile of a user's face, a user is presented 1110 (on computer) with either default feature characteristics, optimal feature characteristics, or a combination thereof. The user then selects 1106 a feature characteristic to change. For example, the default suggestion for the support assembly coupling type characteristic may be double slots 90G coupling. The user instead is allowed to select 1106 a talon clip 90A coupling making the coupling a "custom support assembly mechanical couplings 80," i.e., a custom feature 60. It is understood that computer is structured to present the user with each feature that may be customized and present the user with each available customizable characteristic. For example, for a support assembly coupling, the user is presented with a choice, e.g., a pull down menu, selectable pictures, or any known method of providing a user a selection, of couplings such as talon clips 90A, back-pack clips 90B, magnetic clips 90C, keyed-slot clips 90D, snaps 90E, slots 90F, and double slots 90G.

As used herein, when a user selects any characteristic of a respiratory interface device feature, that feature becomes a "custom feature." Thus, for example and as used herein, a user may accept 1102, 1104 all but one default and/or optimal feature characteristic(s) and then select 1106 one characteristic of one feature, thereby making that feature a custom feature 60 and making respiratory interface device 10 a respiratory interface device 10 including a number of custom features 60.

Thus, selecting 1100 the characteristics for a number of custom features 60 includes allowing the user to select 1112 the characteristics for a number of support assembly couplings, e.g., selecting 1114 characteristics for a number of support assembly couplings, the support assembly coupling component characteristics selected from the group including a location characteristic, a type characteristic, a number characteristic, a contour characteristic, and a visibility characteristic. In an exemplary embodiment, allowing the user to select 1112 the characteristics for a number of coupling assemblies includes allowing the user to select 1118 a right contoured coupling component body 110 contoured to correspond to a specific user's right facial contour, and, allowing the user to select 1119 a left contoured coupling component body 112 contoured to correspond to a specific user's left facial contour.

Selecting 1100 the characteristics for a number of custom features 60 further includes allowing the user to select 1120 the characteristics for a number of fluid couplings, e.g., selecting 1122 characteristics for a number of fluid couplings, the fluid coupling component characteristics selected from the group including a type characteristic, a location characteristic, an orientation characteristic, and a visibility characteristic. By way of example, computer may include a default location characteristic for a fluid coupling in the upper location; the user may select 1122 the lower location as the location characteristic.

Further, selecting 1100 the characteristics for a number of custom features 60 further includes adjusting 1140 other feature selectable characteristics in response to the user's selection of a number of custom feature characteristics. For example, as shown in FIGS. 9A and 9B, upon user selecting to add additional custom support assembly mechanical couplings 80, the location of default support assembly couplings 81 are adjusted downwardly as indicated by the arrows. Thus, former default support assembly couplings 81 are now custom support assembly mechanical couplings 80. As used herein, "other feature selectable characteristics" means the feature characteristics of the features that the user did not select, i.e., the default and/or optimal characteristics the user accepted. That is, in an exemplary embodiment, upon selecting 1100 the characteristics for a number of custom features, the characteristics for other features are also adjusted 1140, thereby making those feature characteristics "custom characteristics." For example, if a user selects 1100 certain custom support assembly couplings type characteristic, e.g., a talon clip 90A, the other support assembly couplings are adjusted to be talon clip 90A as well. It is understood the user may also individually select the characteristics for each respiratory interface device feature. That is, for example, the user may select one support assembly coupling to be a talon clip 90A and another to be a back-pack clip 90B. Thus, after the initial selection 1100 of a custom characteristic for a selected respiratory interface device feature, a user's subsequent selection 1100' of a different custom characteristic for the same selected respiratory interface device feature does not result in the adjusting 1140 other feature selectable characteristics in response to the user's selection.

Producing 1200 respiratory interface device 10 with selected custom features 60 includes producing 1210 respiratory interface device 10 with selected custom features 60 on faceplate medial portion 16. Producing 1200 respiratory interface device 10 with the selected custom features 60 also includes fabricating 1220 respiratory interface device 10 with the selected custom features 60 by 3D printing. Producing 1200 respiratory interface device 10 with the selected custom features 60 also includes fabricating 1220 one of, or both, support 19 that extends between faceplate medial portion 16 and forehead pad 15 and/or custom fluid coupling inlet element 126, wherein support 19 and/or custom fluid coupling inlet element 126 is a low visibility element. In an alternate embodiment, support 19 and/or custom fluid coupling inlet element 126 are fabricated as an intermediate visibility element or a high visibility element.

It can be appreciated that the present invention provides a respiratory interface device that includes custom features, i.e., respiratory interface device features with custom characteristics.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of making a respiratory interface device including a faceplate and custom features comprising:
   acquiring a 3D surface profile of a user's face;
   presenting a number of default or optimal feature characteristics;
   selecting custom feature characteristics for a number of custom features by changing one or more of the number of default or optimal feature characteristics; and
   producing the respiratory interface device including custom features with the selected custom feature characteristics,
   wherein selecting custom feature characteristics for the number of custom features includes:
      allowing the user to accept a default suggestion for each feature characteristic;
      allowing the user to accept an optimal suggestion for each feature characteristic;
      allowing the user to select a number of custom feature characteristics; and
      adjusting other feature selectable characteristics in response to the user's selection of the number of custom feature characteristics, wherein the other feature selectable characteristics are feature characteristics for which the user accepted the default or the optimal suggestion.

2. The method of claim 1 wherein selecting custom feature characteristics for the number of custom features includes allowing the user to select custom feature characteristics for a number of support assembly couplings, the support assembly coupling characteristics selected from the group including a location characteristic, a type characteristic, a number characteristic, a contour characteristic, and a visibility characteristic.

3. The method of claim 1 wherein selecting custom feature characteristics for the number of custom features includes allowing the user to select custom feature characteristics for a number of fluid couplings, the fluid coupling characteristics selected from the group including a type characteristic, a location characteristic, an orientation characteristic, and a visibility characteristic.

4. The method of claim 1 wherein producing the respiratory interface device including custom features with the selected custom feature characteristics includes fabricating the respiratory interface device with the selected custom features by 3D printing.

5. The method of claim 1 wherein the user has a right facial contour and a left facial contour and wherein selecting custom feature characteristics for the number of custom features includes:
   allowing the user to select a right contoured coupling component body contoured to correspond to a specific user's right facial contour; and
   allowing the user to select a left contoured coupling component body contoured to correspond to a specific user's left facial contour.

\* \* \* \* \*